United States Patent
Franceschetti et al.

(10) Patent No.: US 10,105,092 B2
(45) Date of Patent: Oct. 23, 2018

(54) DETECTING SLEEPING DISORDERS

(71) Applicant: Eight Sleep Inc., New York, NY (US)

(72) Inventors: Matteo Franceschetti, New York, NY (US); Massimo Andreasi Bassi, New York, NY (US)

(73) Assignee: Eight Sleep Inc., New York, NY (US)

( * ) Notice: Subject to any disclaimer, the term of this patent is extended or adjusted under 35 U.S.C. 154(b) by 0 days.

(21) Appl. No.: 15/178,117

(22) Filed: Jun. 9, 2016

(65) Prior Publication Data

US 2017/0135632 A1    May 18, 2017

Related U.S. Application Data

(63) Continuation-in-part of application No. 14/942,458, filed on Nov. 16, 2015.

(51) Int. Cl.
| | |
|---|---|
| *A61B 5/00* | (2006.01) |
| *A61B 5/0205* | (2006.01) |
| *A61B 5/11* | (2006.01) |
| *A61B 5/117* | (2016.01) |
| *A61G 7/002* | (2006.01) |
| *A61G 7/015* | (2006.01) |

(Continued)

(52) U.S. Cl.
CPC .......... *A61B 5/4836* (2013.01); *A61B 5/0205* (2013.01); *A61B 5/11* (2013.01); *A61B 5/117* (2013.01); *A61B 5/4818* (2013.01); *A61B 5/725* (2013.01); *A61B 5/7225* (2013.01); *A61B 5/7271* (2013.01); *A61B 5/74* (2013.01); *A61G 7/002* (2013.01); *A61G 7/015* (2013.01); *A61B 5/024* (2013.01); *A61B 5/0816* (2013.01)

(58) Field of Classification Search
CPC ... A61B 5/4815; A61B 5/4806; A61B 5/4809; A61B 5/4812; A61B 5/4818
See application file for complete search history.

(56) References Cited

U.S. PATENT DOCUMENTS

| | | |
|---|---|---|
| 4,136,685 A | 1/1979 | Ramey |
| 4,299,233 A | 11/1981 | Lemelson |

(Continued)

FOREIGN PATENT DOCUMENTS

| | | |
|---|---|---|
| CN | 103519597 A | 1/2014 |
| CN | 103945802 A | 7/2014 |

(Continued)

OTHER PUBLICATIONS

International Search Report and Written Opinion dated Aug. 18, 2016 of PCT/US2016/031060, filed May 5, 2016. (7 pages).

(Continued)

*Primary Examiner* — Eric J Kurilla
(74) *Attorney, Agent, or Firm* — Wilson Sonsini Goodrich & Rosati

(57) ABSTRACT

Introduced are methods and systems for monitoring a person's sleeping patterns, and detecting episodes of sleeping disorders such as snoring and sleep apnea. In one embodiment, a sensor strip attached to the mattress monitors the user's breathing, and detects signature frequencies corresponding to snoring and sleep apnea. Once a sleeping disorder is detected, a notification can be sent to a device associated with the user, or the user's bed can be automatically adjusted to alleviate the sleeping disorder.

11 Claims, 34 Drawing Sheets

(51) Int. Cl.
  *A61B 5/08*   (2006.01)
  *A61B 5/024*  (2006.01)

(56) References Cited

U.S. PATENT DOCUMENTS

| | | | |
|---|---|---|---|
| 4,440,177 A * | 4/1984 | Anderson | A61B 5/083 |
| | | | 128/205.12 |
| 5,157,372 A | 10/1992 | Langford | |
| 5,307,051 A | 4/1994 | Sedlmayr | |
| 5,319,363 A | 6/1994 | Welch et al. | |
| 5,353,788 A | 10/1994 | Miles | |
| 5,435,317 A | 7/1995 | McMahon et al. | |
| 5,479,939 A | 1/1996 | Ogino | |
| 5,902,255 A | 5/1999 | Ogino | |
| 5,948,303 A | 9/1999 | Larson | |
| 5,949,303 A | 9/1999 | Arvidsson et al. | |
| 6,045,514 A | 4/2000 | Raviv et al. | |
| 6,236,621 B1 | 5/2001 | Schettino et al. | |
| 6,254,545 B1 | 7/2001 | Stasz et al. | |
| 6,485,432 B1 | 11/2002 | Stasz et al. | |
| 6,491,642 B1 | 12/2002 | Stasz et al. | |
| 6,547,728 B1 | 4/2003 | Cornuejols et al. | |
| 6,551,256 B1 | 4/2003 | Stasz et al. | |
| 6,702,755 B1 | 3/2004 | Stasz et al. | |
| 6,765,489 B1 | 7/2004 | Ketelhohn et al. | |
| 6,774,795 B2 | 8/2004 | Eshelman et al. | |
| 6,784,826 B2 | 8/2004 | Kane et al. | |
| 6,825,769 B2 | 11/2004 | Colmenarez et al. | |
| 6,888,453 B2 | 5/2005 | Lutz et al. | |
| 6,890,304 B1 | 5/2005 | Uebaba et al. | |
| 7,089,099 B2 | 8/2006 | Shostak et al. | |
| 7,202,791 B2 | 4/2007 | Trajkovic | |
| 7,289,036 B2 | 10/2007 | Salzhauer et al. | |
| 7,369,680 B2 | 5/2008 | Strubbe et al. | |
| 7,372,370 B2 | 5/2008 | Stults et al. | |
| 7,461,422 B1 | 12/2008 | Baker et al. | |
| 7,734,334 B2 | 6/2010 | Mietus et al. | |
| 7,825,813 B2 | 11/2010 | Farhan et al. | |
| 7,868,757 B2 | 1/2011 | Radivojevic et al. | |
| 7,883,480 B2 | 2/2011 | Dunlop et al. | |
| 8,035,508 B2 | 10/2011 | Breed et al. | |
| 8,147,407 B2 | 4/2012 | Moore et al. | |
| 8,147,420 B2 | 4/2012 | Henke et al. | |
| 8,292,819 B2 | 10/2012 | Kuo et al. | |
| 8,337,431 B2 | 12/2012 | Heruth et al. | |
| 8,348,840 B2 | 1/2013 | Heit et al. | |
| 8,355,769 B2 | 1/2013 | Popovic et al. | |
| 8,410,942 B2 | 4/2013 | Chacon et al. | |
| 8,410,943 B2 | 4/2013 | Metz et al. | |
| 8,427,311 B2 | 4/2013 | Schlangen et al. | |
| 8,444,558 B2 | 5/2013 | Young et al. | |
| 8,461,996 B2 | 6/2013 | Gallagher et al. | |
| 8,493,220 B2 | 7/2013 | Virtanen et al. | |
| 8,512,221 B2 | 8/2013 | Kaplan et al. | |
| 8,523,758 B1 | 9/2013 | Kirby et al. | |
| 8,525,680 B2 | 9/2013 | Ribble et al. | |
| 8,628,462 B2 | 1/2014 | Berka et al. | |
| 8,628,478 B2 | 1/2014 | Conte et al. | |
| 8,641,616 B2 | 2/2014 | Shirai et al. | |
| 8,672,853 B2 | 3/2014 | Young et al. | |
| 8,692,677 B2 | 4/2014 | Wada et al. | |
| 8,698,635 B2 | 4/2014 | Epperson et al. | |
| 8,755,879 B2 | 6/2014 | Hang et al. | |
| 8,766,805 B2 | 7/2014 | Alameh et al. | |
| 8,803,366 B2 | 8/2014 | Proud | |
| 8,803,682 B2 | 8/2014 | Wong et al. | |
| 8,810,430 B2 | 8/2014 | Proud | |
| 8,836,516 B2 | 9/2014 | Wolfe et al. | |
| 8,850,421 B2 | 9/2014 | Proud | |
| 8,852,127 B2 | 10/2014 | Bell et al. | |
| 8,866,621 B2 | 10/2014 | Conte et al. | |
| 8,876,737 B2 | 11/2014 | Prendergast et al. | |
| 8,880,137 B2 | 11/2014 | Tomasco et al. | |
| 8,880,207 B2 | 11/2014 | Karunajeewa et al. | |
| 8,893,329 B2 | 11/2014 | Petrovski et al. | |
| 8,932,199 B2 | 1/2015 | Popovic et al. | |
| 8,933,809 B2 | 1/2015 | Emori et al. | |
| 8,939,884 B2 | 1/2015 | Kashima et al. | |
| 8,948,861 B2 | 2/2015 | Kalik et al. | |
| 8,961,413 B2 | 2/2015 | Liden et al. | |
| 8,979,730 B2 | 3/2015 | Rademaker et al. | |
| 8,988,014 B2 | 3/2015 | Noguchi et al. | |
| 9,000,931 B2 | 4/2015 | Tomimori et al. | |
| 9,011,347 B2 | 4/2015 | Addison et al. | |
| 9,186,479 B1 | 11/2015 | Franceschetti et al. | |
| 9,232,910 B2 | 1/2016 | Alshaer et al. | |
| 9,370,457 B2 | 6/2016 | Nunn et al. | |
| 2002/0015740 A1 | 2/2002 | Ackman et al. | |
| 2002/0080035 A1 | 6/2002 | Youdenko et al. | |
| 2002/0128700 A1 | 9/2002 | Cross, Jr. et al. | |
| 2003/0159219 A1 | 8/2003 | Harrison et al. | |
| 2003/0195140 A1 | 10/2003 | Ackman et al. | |
| 2005/0190065 A1 | 9/2005 | Ronnholm et al. | |
| 2006/0162074 A1 | 7/2006 | Bader | |
| 2006/0173257 A1 | 8/2006 | Nagai et al. | |
| 2006/0293608 A1 | 12/2006 | Rothman et al. | |
| 2007/0282215 A1 | 12/2007 | Ni et al. | |
| 2008/0027337 A1 | 1/2008 | Dugal et al. | |
| 2008/0155750 A1 | 7/2008 | Mossbeck et al. | |
| 2008/0157956 A1 | 7/2008 | Radivojevic et al. | |
| 2008/0169931 A1 | 7/2008 | Gentry et al. | |
| 2008/0275349 A1 | 11/2008 | Halperin et al. | |
| 2009/0105560 A1 | 4/2009 | Solomon et al. | |
| 2009/0105605 A1 | 4/2009 | Abreu et al. | |
| 2010/0076252 A1 | 3/2010 | Henke et al. | |
| 2011/0010014 A1 | 1/2011 | Oexman et al. | |
| 2011/0034811 A1 | 2/2011 | Naujokat et al. | |
| 2011/0112442 A1 | 5/2011 | Meger et al. | |
| 2011/0115635 A1 | 5/2011 | Petrovski et al. | |
| 2011/0156915 A1 | 6/2011 | Brauers et al. | |
| 2011/0267196 A1 | 11/2011 | Hu et al. | |
| 2011/0295083 A1 | 12/2011 | Doelling et al. | |
| 2012/0092171 A1 | 4/2012 | Hwang et al. | |
| 2012/0103556 A1 | 5/2012 | Lee et al. | |
| 2012/0119886 A1 | 5/2012 | Rawls-Meehan et al. | |
| 2012/0138067 A1 * | 6/2012 | Rawls-Meehan | A47C 20/041 |
| | | | 128/845 |
| 2012/0143095 A1 | 6/2012 | Nakamura et al. | |
| 2012/0210513 A1 | 8/2012 | Chestakov et al. | |
| 2012/0251989 A1 | 10/2012 | Wetmore et al. | |
| 2013/0144190 A1 | 6/2013 | Bruce et al. | |
| 2013/0234823 A1 | 9/2013 | Kahn et al. | |
| 2013/0245502 A1 | 9/2013 | Lange et al. | |
| 2013/0276234 A1 | 10/2013 | Rawls-Meehan et al. | |
| 2013/0282198 A1 | 10/2013 | Kneuer et al. | |
| 2014/0116440 A1 | 5/2014 | Thompson et al. | |
| 2014/0257573 A1 | 9/2014 | Van De Sluis et al. | |
| 2014/0259418 A1 | 9/2014 | Nunn et al. | |
| 2014/0278229 A1 | 9/2014 | Hong et al. | |
| 2014/0323799 A1 | 10/2014 | Van Driel et al. | |
| 2014/0343889 A1 | 11/2014 | Shalom et al. | |
| 2014/0345060 A1 | 11/2014 | Ribble et al. | |
| 2015/0073306 A1 | 3/2015 | Abeyratne et al. | |
| 2015/0112155 A1 | 4/2015 | Bijjani et al. | |
| 2015/0120205 A1 | 4/2015 | Jeon et al. | |
| 2015/0128353 A1 | 5/2015 | Kildey | |
| 2015/0136146 A1 | 5/2015 | Hood et al. | |
| 2015/0137994 A1 | 5/2015 | Rahman et al. | |
| 2015/0164438 A1 | 6/2015 | Halperin et al. | |
| 2015/0164721 A1 | 6/2015 | Miyashita et al. | |
| 2015/0173672 A1 * | 6/2015 | Goldstein | A61B 5/4818 |
| | | | 600/301 |
| 2015/0182305 A1 | 7/2015 | Lowe et al. | |
| 2015/0199919 A1 | 7/2015 | Ander et al. | |
| 2015/0230750 A1 | 8/2015 | McDarby et al. | |
| 2015/0320588 A1 | 11/2015 | Connor et al. | |
| 2015/0335507 A1 | 11/2015 | Emmons et al. | |
| 2015/0342519 A1 | 12/2015 | Zheng | |
| 2015/0351556 A1 | 12/2015 | Franceschetti et al. | |
| 2015/0351700 A1 | 12/2015 | Franceschetti et al. | |
| 2015/0352313 A1 | 12/2015 | Franceschetti et al. | |
| 2015/0355605 A1 | 12/2015 | Franceschetti et al. | |
| 2015/0355612 A1 | 12/2015 | Franceschetti et al. | |
| 2015/0366365 A1 | 12/2015 | Golin et al. | |

(56) References Cited

U.S. PATENT DOCUMENTS

| | | |
|---|---|---|
| 2016/0015315 A1 | 1/2016 | Auphan et al. |
| 2016/0073788 A1 | 3/2016 | Franceschetti et al. |
| 2016/0073950 A1 | 3/2016 | Franceschetti et al. |
| 2016/0093196 A1 | 3/2016 | Shinar et al. |
| 2016/0120716 A1 | 5/2016 | Ribble et al. |
| 2016/0128488 A1 | 5/2016 | Franceschetti et al. |
| 2016/0136383 A1 | 5/2016 | Franceschetti et al. |
| 2016/0151603 A1 | 6/2016 | Shouldice et al. |
| 2016/0192886 A1 | 7/2016 | Nunn et al. |
| 2016/0310697 A1 | 10/2016 | Franceschetti et al. |
| 2017/0028165 A1 | 2/2017 | Franceschetti et al. |
| 2017/0135881 A1 | 5/2017 | Franceschetti et al. |
| 2017/0135882 A1 | 5/2017 | Franceschetti et al. |
| 2017/0135883 A1 | 5/2017 | Franceschetti et al. |
| 2017/0259028 A1 | 9/2017 | Franceschetti et al. |
| 2017/0296773 A1 | 10/2017 | Franceschetti et al. |

FOREIGN PATENT DOCUMENTS

| | | |
|---|---|---|
| FR | 2788595 A1 | 7/2000 |
| JP | 2004154242 A | 6/2004 |
| JP | 2008000222 A | 1/2008 |
| JP | 2008279193 A | 11/2008 |
| KR | 20150003987 A | 1/2015 |
| WO | 2013134160 A2 | 9/2013 |
| WO | WO-2017087023 A1 | 5/2017 |
| WO | WO-2017213732 A1 | 12/2017 |

OTHER PUBLICATIONS

Non-Final Office Action dated Aug. 31, 2016 of U.S. Appl. No. 15/178,124 by Franceschetti, M., et al., filed Jun. 9, 2016.
U.S. Appl. No. 14/732,608 of Franceschetti, M., et al., filed Jun. 5, 2015.
U.S. Appl. No. 14/732,624 of Franceschetti, M., et al., filed Jun. 5, 2015.
U.S. Appl. No. 14/732,638 of Franceschetti, M., et al., filed Jun. 5, 2015.
U.S. Appl. No. 14/732,643 of Franceschetti, M., et al., filed Jun. 5, 2015.
U.S. Appl. No. 14/732,646 of Franceschetti, M., et al., filed Jun. 5, 2015.
U.S. Appl. No. 14/946,496 of Franceschetti, M., et al., filed Nov. 19, 2015.
U.S. Appl. No. 14/947,685 of Franceschetti, M., et al., filed Nov. 20, 2015.
U.S. Appl. No. 14/969,932 of Franceschetti, M., et al., filed Dec. 15, 2015.
U.S. Appl. No. 14/969,902 of Franceschetti, M., et al., filed Dec. 15, 2015.
International Search Report and Written Opinion dated Jul. 14, 2016, for International Application No. PCT/US2016/030594, 7 pages.
International Search Report and Written Opinion dated Sep. 24, 2015, for International Patent Application No. PCT/US2015/034574, 7 pages.
Non-Final Office Action dated Apr. 15, 2016, for U.S. Appl. No. 14/946,496 of Franceschetti, M., et al., filed Nov. 19, 2015.
Non-Final Office Action dated Aug. 31, 2015 for U.S. Appl. No. 14/732,608 by Franceschetti, M., et al., filed Jun. 5, 2015.
Non-Final Office Action dated Jun. 1, 2016 of U.S. Appl. No. 14/969,932 by Franceschetti, M., et al., filed Dec. 15, 2015.
Non-Final Office Action dated Jun. 13, 2016, for U.S. Appl. No. 14/969,902 of Franceschetti, M. et al. filed Dec. 15, 2015.
Notice of Allowance dated Oct. 7, 2015, for U.S. Appl. No. 14/732,608 by Franceschetti, M., et al., filed Jun. 5, 2015.
U.S. Appl. No. 14/942,458 of Franceschetti, M. filed Nov. 16, 2015.
U.S. Appl. No. 14/942,509 of Franceschetti, M. filed Nov. 16, 2015.
U.S. Appl. No. 15/178,124 of Franceschetti, M. et al. filed Jun. 9, 2016.
U.S. Appl. No. 15/178,132 of Franceschetti, M. et al. filed Jun. 9, 2016.
Cavusoglu, M., et al., "Spectral Envelope Analysis of Snoring Signals," Proceedings of the Sixth IASTED International Conference, Biomedical Engineering, Feb. 13-15, 2008, Innsbruck Austria, pp. 473-477.
U.S. Appl. No. 15/602,969 of Franceschetti, M., et al., filed May 23, 2017.
Final Office Action dated Jun. 8, 2017 of U.S. Appl. No. 17/732,624 by Franceschetti, M., et al., filed Jun. 5, 2015.
Final Office Action dated Nov. 23, 2016 for U.S. Appl. No. 14/969,902 by Franceschetti, M., et al., filed Dec. 15, 2015.
Final Office Action dated Oct. 11, 2016, for U.S. Appl. No. 14/946,496 of Franceschetti, M., et al., filed Nov. 19, 2015.
International Search Report and Written Opinion dated Aug. 25, 2016 for International Application No. PCT/US2016/031054, filed May 5, 2016. (8 pages).
International Search Report and Written Opinion dated Sep. 29, 2016 for International Application No. PCT/US2016/029889, filed Apr. 28, 2016. (7 pages).
Non-Final Office Action dated Apr. 3, 2017 of U.S. Appl. No. 14/732,646 of Franceschetti, M., et al., filed Jun. 5, 2015.
Non-Final Office Action dated Dec. 13, 2016 for U.S. Appl. No. 14/942,458 by Franceschetti, M., et al., filed Nov. 16, 2015.
Non-Final Office Action dated Dec. 16, 2016 for U.S. Appl. No. 15/178,132 of Franceschetti, M., et al. filed Jun. 9, 2016.
Non-Final Office Action dated May 23, 2017 of U.S. Appl. No. 14/732,643 of Franceschetti, M., et al., filed Jun. 5, 2015.
Non-Final Office Action dated Oct. 19, 2016 of U.S. Appl. No. 14/732,624 of Franceschetti, M., et al., filed Jun. 5, 2015.
Notice of Allowance dated Dec. 27, 2016 for U.S. Appl. No. 15/178,124 by Franceschetti, M., et al., filed Jun. 9, 2016.
Notice of Allowance dated May 24, 2017 for U.S. Appl. No. 15/178,124 by Franceschetti, M., et al., filed Jun. 9, 2016.
Notice of Allowance dated Oct. 18, 2016, for U.S. Appl. No. 14/969,932 by Franceschetti, M., et al., filed Dec. 15, 2015.
Restriction Requirement dated Apr. 17, 2017 of U.S. Appl. No. 14/732,638 by Franceschetti, M., et al., filed Jun. 5, 2015.
U.S. Appl. No. 15/293,049 of Franceschetti, M.,. et al., filed Oct. 13, 2016.
International Search Report and Written Opinion dated Sep. 29, 2016 for International Patent Application No. PCT/US2016/031062, filed May 5, 2016. (8 pages).
Final Office Action dated Dec. 21, 2017 for U.S. Appl. No. 14/732,646 of Franceschetti, M., et al., filed Jun. 5, 2015.
Final Office Action dated Dec. 26, 2017 for U.S. Appl. No. 14/732,643 of Franceschetti, M., et al., filed Jun. 5, 2015.
Non-Final Office Action dated Dec. 8, 2017 for U.S. Appl. No. 14/942,509 of Franceschetti, M. filed Nov. 16, 2015.
Supplemental Notice of Allowability dated Jan. 13, 2017 for U.S. Appl. No. 14/969,932 of Franceschetti, M. et al. filed Dec. 15, 2015.
Non-Final Office Action dated Jun. 23, 2017 of U.S. Appl. No. 14/946,496 of Franceschetti, M., et al., filed Nov. 19, 2015.
Non-Final Office Action dated Jun. 27, 2017 for U.S. Appl. No. 14/732,638 of Franceschetti, M. et al. filed Jun. 5, 2015.
Non-Final Office Action dated Aug. 2, 2017 for U.S. Appl. No. 14/969,902 of Franceschetti, M., et al., filed Dec. 15, 2015.
International Search Report and Written Opinion dated Aug. 14, 2017 for International Application No. PCT/US2017/024370, 8 pages.
Final Office Action dated Sep. 7, 2017 for U.S. Appl. No. 14/942,458 of Franceschetti, M., et al., filed Nov. 16, 2015.
Final Office Action dated Sep. 11, 2017 of U.S. Appl. No. 15/178,132 by Franceschetti, M., et al., filed Jun. 9, 2016.

* cited by examiner

DETECTING SLEEPING DISORDERS

CROSS-REFERENCE TO RELATED APPLICATIONS

This application is a continuation-in-part of the U.S. patent application Ser. No. 14/942,458 filed Nov. 16, 2015, which is incorporated herein by reference in its entirety.

TECHNICAL FIELD

Various embodiments relate generally to home automation devices and human biological signal gathering and analysis.

BACKGROUND

Sleeping disorders can vary from mild to severe, and include snoring, restless leg, and sleep apnea. Most sleeping disorder sufferers do not have an in-home method of monitoring their sleeping patterns, much less a way to regulate and alleviate the sleeping disorders.

SUMMARY

Introduced are methods and systems for monitoring a person's sleeping patterns, and detecting episodes of sleeping disorders such as snoring and sleep apnea. In one embodiment, a sensor strip attached to the mattress monitors the user's breathing, and detects signature frequencies corresponding to snoring and sleep apnea. Once a sleeping disorder is detected, a notification can be sent to a device associated with the user, or the user's bed can be automatically adjusted to alleviate the sleeping disorder.

BRIEF DESCRIPTION OF THE DRAWINGS

These and other objects, features and characteristics of the present embodiments will become more apparent to those skilled in the art from a study of the following detailed description in conjunction with the appended claims and drawings, all of which form a part of this specification. While the accompanying drawings include illustrations of various embodiments, the drawings are not intended to limit the claimed subject matter.

DETAILED DESCRIPTION

Figure 1:
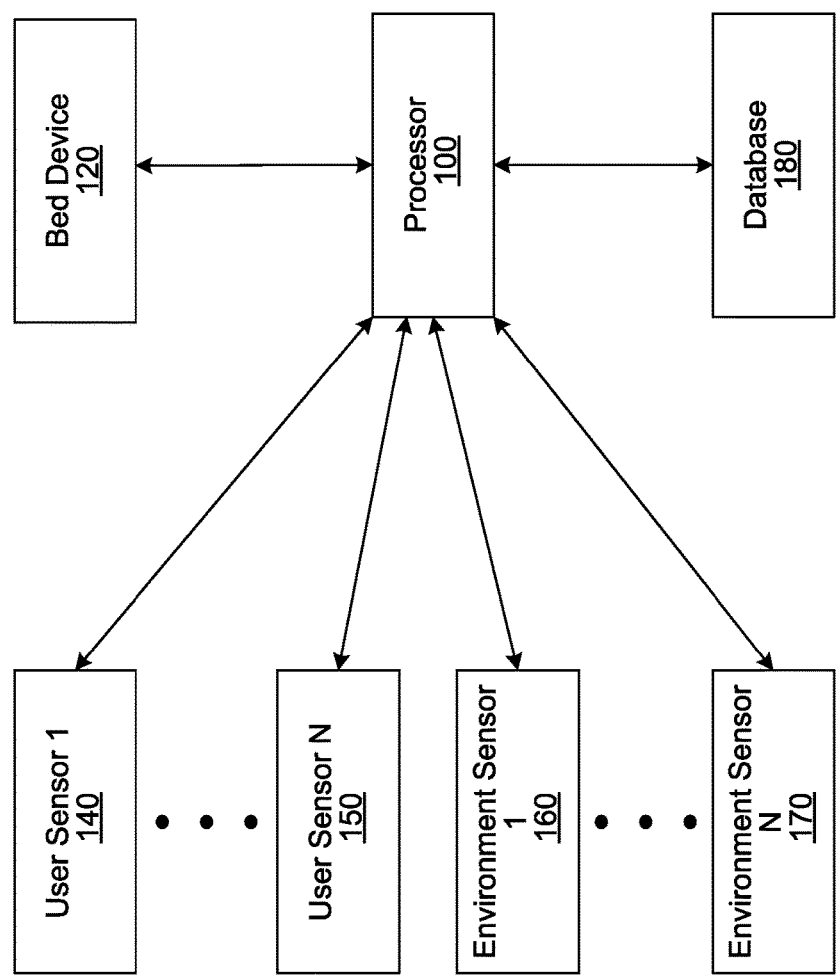
FIG. 1 is a diagram of a bed device, according to one embodiment.

Examples of a method, apparatus, and computer program for automating the control of home appliances and improving the sleep environment are disclosed below. In the following description, for the purposes of explanation, numerous specific details are set forth in order to provide a thorough understanding of the embodiments of the invention. One skilled in the art will recognize that the embodiments of the invention may be practiced without these specific details or with an equivalent arrangement. In other instances, well-known structures and devices are shown in block diagram form in order to avoid unnecessarily obscuring the embodiments of the invention.

Terminology

Brief definitions of terms, abbreviations, and phrases used throughout this application are given below.

In this specification, the terms "biological signal" and "bio signal" are synonyms, and are used interchangeably.

Reference in this specification to "sleep phase" means light sleep, deep sleep, or REM sleep. Light sleep comprises stage one, and stage two, non-REM sleep.

Reference in this specification to a formant means the spectral peaks of the sound spectrum.

Reference in the specification to a formant bandwidth means a continuous frequency region in which the amplification differs less than 3 dB from the amplification at the center frequency (the frequency where the amplification is maximal).

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described that may be exhibited by some embodiments and not by others. Similarly, various requirements are described that may be requirements for some embodiments but not others.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements. The coupling or connection between the elements can be physical, logical, or a combination thereof. For example, two devices may be coupled directly, or via one or more intermediary channels or devices. As another example, devices may be coupled in such a way that information can be passed therebetween, while not sharing any physical connection with one another. Additionally, the words "herein," "above," "below," and words of similar import, when used in this application, shall refer to this application as a whole and not to any particular portions of this application. Where the context permits, words in the Detailed Description using the singular or plural number may also include the plural or singular number respectively. The word "or," in reference to a list of two or more items, covers all of the following interpretations of the word: any of the items in the list, all of the items in the list, and any combination of the items in the list.

If the specification states a component or feature "may," "can," "could," or "might" be included or have a characteristic, that particular component or feature is not required to be included or have the characteristic.

The term "module" refers broadly to software, hardware, or firmware components (or any combination thereof). Modules are typically functional components that can generate useful data or another output using specified input(s). A module may or may not be self-contained. An application program (also called an "application") may include one or more modules, or a module may include one or more application programs.

The terminology used in the Detailed Description is intended to be interpreted in its broadest reasonable manner, even though it is being used in conjunction with certain examples. The terms used in this specification generally have their ordinary meanings in the art, within the context of the disclosure, and in the specific context where each term is used. For convenience, certain terms may be highlighted, for example, using capitalization, italics, and/or quotation marks. The use of highlighting has no influence on the scope and meaning of a term; the scope and meaning of a term is the same, in the same context, whether or not it is highlighted. It will be appreciated that the same element can be described in more than one way.

Consequently, alternative language and synonyms may be used for any one or more of the terms discussed herein, but special significance is not to be placed upon whether or not a term is elaborated or discussed herein. A recital of one or more synonyms does not exclude the use of other synonyms. The use of examples anywhere in this specification, including examples of any terms discussed herein, is illustrative only and is not intended to further limit the scope and meaning of the disclosure or of any exemplified term. Likewise, the disclosure is not limited to various embodiments given in this specification.

Bed Device

FIG. 1 is a diagram of a bed device, according to one embodiment. Any number of user sensors 140, 150 monitor the bio signals associated with a user, such as the heart rate, the breathing rate, the temperature, motion, or presence, associated with the user. Any number of environment sensors 160, 170 monitor environment properties, such as temperature, sound, light, or humidity. The user sensors 140, 150 and the environment sensors 160, 170 communicate their measurements to the processor 100. The environment sensors 160, 170 measure the properties of the environment that the environment sensors 160, 170 are associated with. In one embodiment, the environment sensors 160, 170 are placed next to the bed. The processor 100 determines, based on the bio signals associated with the user, historical bio signals associated with the user, user-specified preferences, exercise data associated with the user, or the environment properties received, a control signal, and a time to send the control signal to a bed device 120.

According to one embodiment, the processor 100 is connected to a database 180, which stores the biological signals associated with a user. Additionally, the database 180 can store average biological signals associated with the user, history of biological signals associated with a user, etc. In one embodiment, the database 180 can store a user profile which contains user preferences associated with an adjustable bed frame.

Figure 2A:
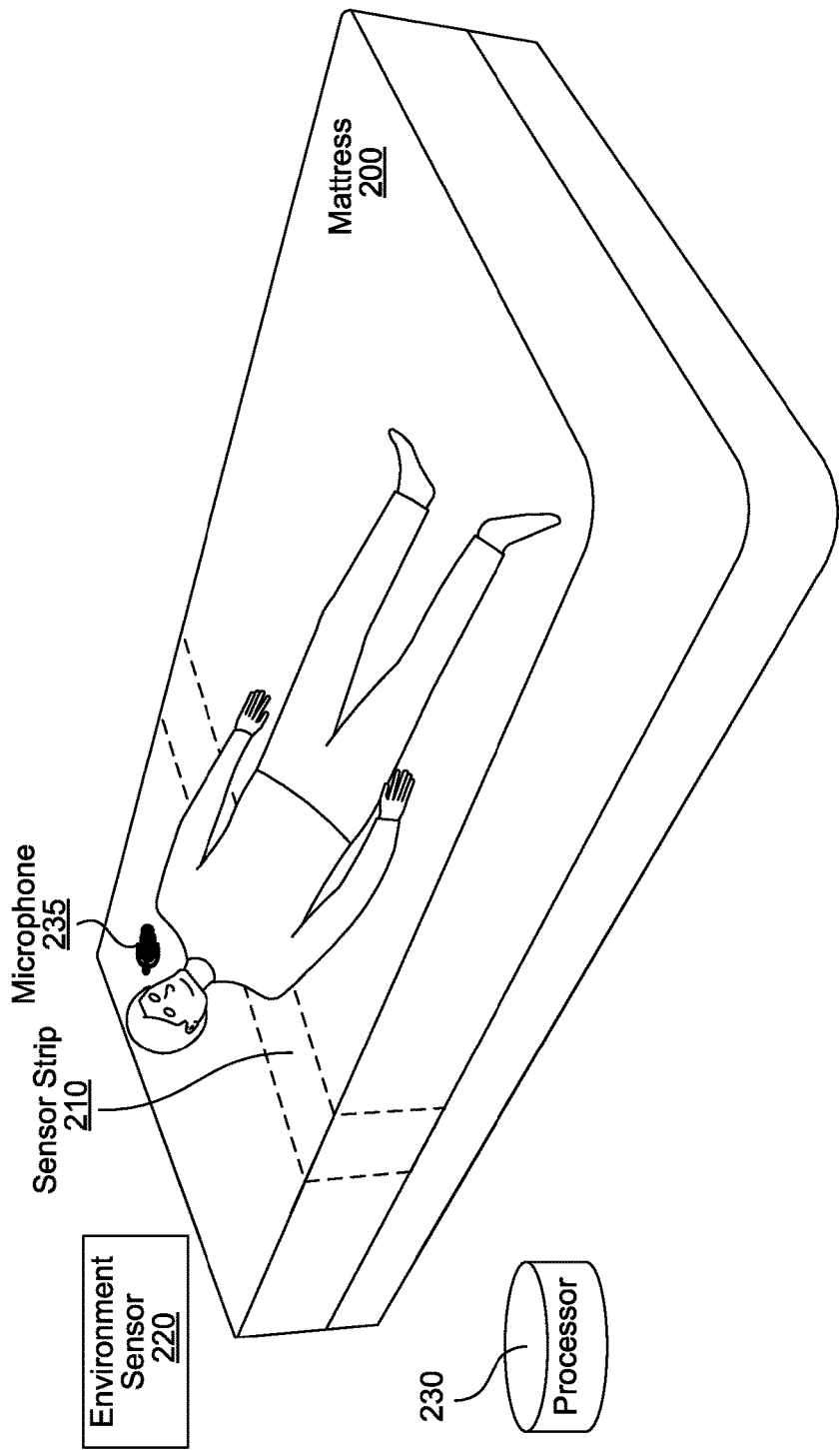
FIG. 2A illustrates an example of a bed device, according to one embodiment.

FIG. 2A illustrates an example of the bed device of FIG. 1, according to one embodiment. A sensor strip 210, associated with a mattress 200 of the bed device 120, monitors bio signals associated with a user sleeping on the mattress 200. The sensor strip 210 can be built into the mattress 200, or can be part of a bed pad device. Alternatively, the sensor strip 210 can be a part of any other piece of furniture, such as a rocking chair, a couch, an armchair, etc. The sensor strip 210 comprises a temperature sensor, or a piezo sensor. The environment sensor 220 measures environment properties such as temperature, sound, light or humidity. According to one embodiment, the environment sensor 220 is associated with the environment surrounding the mattress 200. The sensor strip 210 and the environment sensor 220 communicate the measured environment properties to the processor 230.

A microphone 235 is placed proximate to the user. The microphone 235 records a sound associated with the user. The microphone 235 can be disposed within the mattress 200, a pillow, a cover, the sensor strip 210, the power supply box, etc.

In some embodiments, the processor 230 can be similar to the processor 100 of FIG. 1. A processor 230 can be connected to the sensor strip 210, or the environment sensor 220 by a computer bus, such as an I2C bus. Also, the processor 230 can be connected to the sensor strip 210, or the environment sensor 220 by a communication network. By way of example, the communication network connecting the processor 230 to the sensor strip 210 or the environment sensor 220 includes one or more networks such as a data network, a wireless network, a telephony network, or any combination thereof. The data network may be any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, or any combination thereof. In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, code division multiple access (CDMA), wideband code division multiple access (WCDMA), wireless fidelity (WiFi), wireless LAN (WLAN), Bluetooth®, Internet Protocol (IP) data casting, satellite, mobile ad-hoc network (MANET), and the like, or any combination thereof.

The processor 230 is any type of microcontroller, or any processor in a mobile terminal, fixed terminal, or portable terminal including a mobile handset, station, unit, device, multimedia computer, multimedia tablet, Internet node, cloud computer, communicator, desktop computer, laptop computer, notebook computer, netbook computer, tablet computer, personal communication system (PCS) device, personal navigation device, personal digital assistants (PDAs), audio/video player, digital camera/camcorder, positioning device, television receiver, radio broadcast receiver, electronic book device, game device, the accessories and peripherals of these devices, or any combination thereof.

Figure 2B:
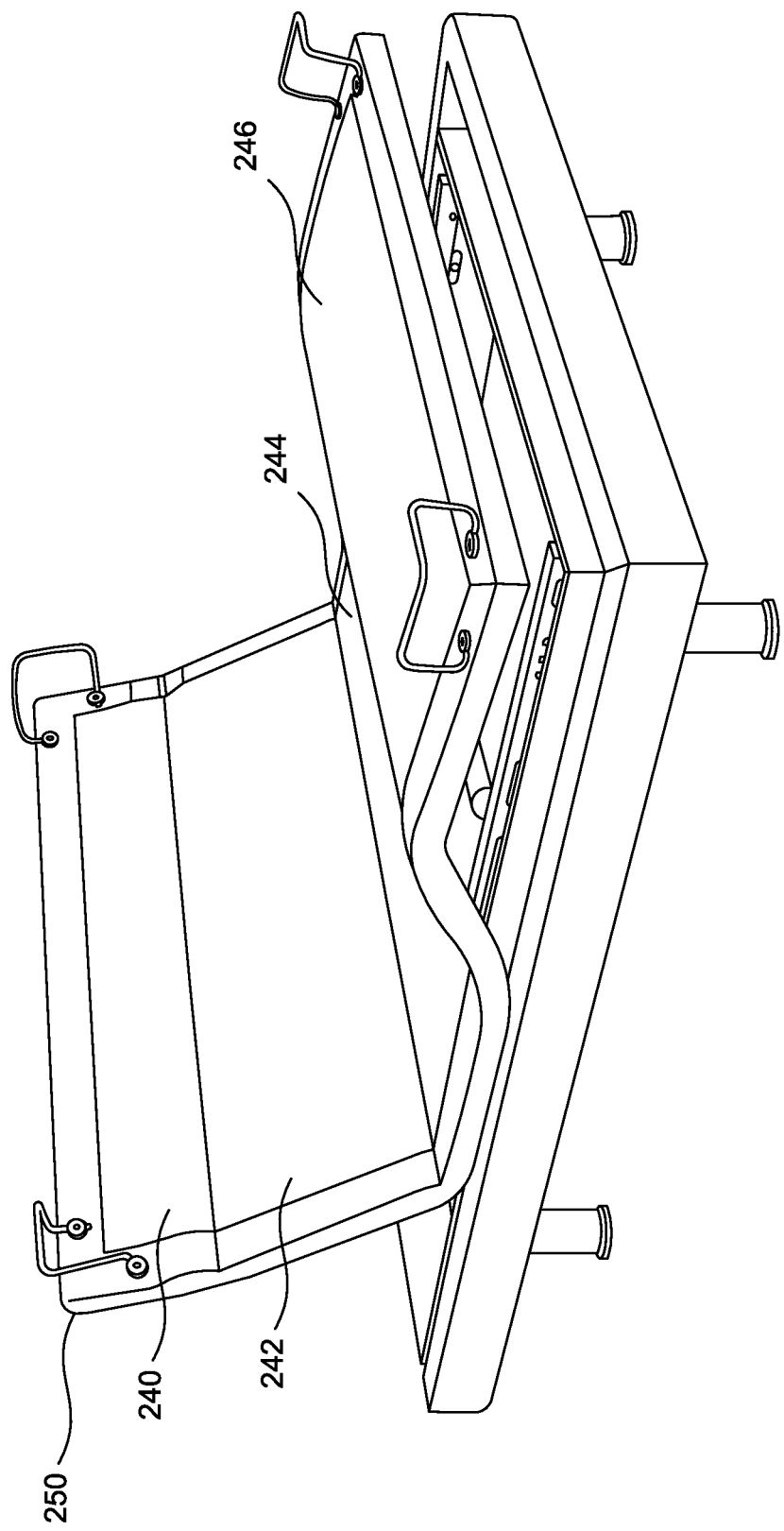
FIG. 2B is an adjustable bed frame associated with the bed device of FIG. 2A, according to one embodiment.

FIG. 2B is an adjustable bed frame 250 associated with the bed device, according to one embodiment. The adjustable bed frame includes a plurality of adjustable sections 240-246. The adjustable bed frame has a rest position, as seen in FIG. 2A, where all the adjustable sections 240-246 are at 0 height, and at 0° angle. The rest position corresponds to the horizontal position of a regular bed. The position associated with each adjustable section 240-246 includes a height relative to the rest position, and an angle relative to the rest position. Adjustable section 240 corresponds to the head, adjustable section 242 corresponds to the back, adjustable section 244 corresponds to the legs, and adjustable section 246 corresponds to the feet. There can be more adjustable sections according to various embodiments. The position of each adjustable section 240-246 can be adjusted independently.

The adjustable bed frame 250 is coupled to the processor 230. The processor 230 is configured to identify the user based on at least one of: the heart rate associated with the user, the breathing rate associated with the user, or the motion associated with the user, because each user has a unique heart rate, breathing rate, and motion. The processor 230 can also identify the user by receiving from a user device associated with the user an identification (ID) associated with the user. For example, the user can specify the user ID of the person sleeping on the sensor strip. If there are multiple sensor strips and/or multiple sensor, the user can specify the ID of the person associated with each sensor strip and/or each sensor. The processor 230, after identifying the user, retrieves from the database 180 a history of biological signals associated with a user. The history of biological signals comprises a normal biological signal range, such as a normal heart rate range associated with said user, a normal breathing rate range associated with said user, and a normal motion range associated with said user. The normal biological signal range includes an average heart rate associated with the user, an average breathing rate associated with the user, and an average motion associated with the user. The average biological signal includes an average high signal and an average low signal. For example, the average high signal includes the average high heart rate associated with the user, the average high breathing rate associated with a user, or the average high rate of motion associated with the user. The average low signal includes the average low heart rate associated with the user, the average low breathing rate associated with a user, or the average low rate of motion associated with a user. In addition, based on the heart rate, the breathing rate, and the motion, the processor 230 determines the sleep phase associated with the user. The processor 230 can then calculate the normal bio signal range associated with a particular sleep phase.

The bio signals associated with a user include an amplitude and a frequency. The processor 230 determines a normal range of frequencies associated with the heart rate, the breathing rate, or the motion. The processor 230 determines a normal range of amplitudes and frequencies associated with the heart rate, the breathing rate or the motion. The processor 230 determines the current amplitude and the current frequency associated with the current biological signal. When the current frequency associated with a biological signal is outside of the normal frequency range, the processor 230 detects a discrepancy. The processor 230 determines which sleeping disorder the discrepancy is indicative of, such as snoring, sleep apnea, or restless leg. For example, the processor 230 can determine whether the breathing rate contains sequences outside of the normal breathing rate frequency range, and determine that the user is snoring. Similarly, the processor 230 can determine that the motion rate contains a frequency outside of the normal motion frequency range, and determine that the user is suffering from restless leg.

When a sleeping disorder is detected, the processor 230 sends a control signal to the adjustable bed frame to heighten or to lower an adjustable section associated with the bed frame. For example, if the processor 230 detects that the user is snoring or has sleep apnea, the processor 230 sends a control signal to the adjustable bed frame to heighten the adjustable section 240, corresponding to the head. If the processor 230 detects that the user has a restless leg, the processor 230 sends a control signal to the adjustable bed frame to heighten the adjustable section 246, corresponding to the feet.

According to another embodiment, the processor 230 determines whether the user has fallen asleep while the bed is in the upright position, for example, when the user has fallen asleep while watching TV. If the user has fallen asleep and the bed is not in the rest position, the processor 230 sends a control signal to the adjustable frame to assume the rest position.

According to one embodiment, the user can specify the preferred position of the adjustable bed frame when a bio signal discrepancy is detected. The user's preferred position is stored in a user profile in the database 180. For example, the user can specify the height and inclination of each of the adjustable sections 240-246 for each detected problem. For example, the user-specified height and inclination of each of the adjustable sections 240-246 when snoring is detected can be different from the user-specified height and inclination of each of the adjustable sections 240-246 when sleep apnea is detected. In addition, a user can specify a rest position for the adjustable bed frame that is different from the default horizontal rest position. The user-specified rest position can also be associated with the user profile and stored in the database 180.

Figure 2C:
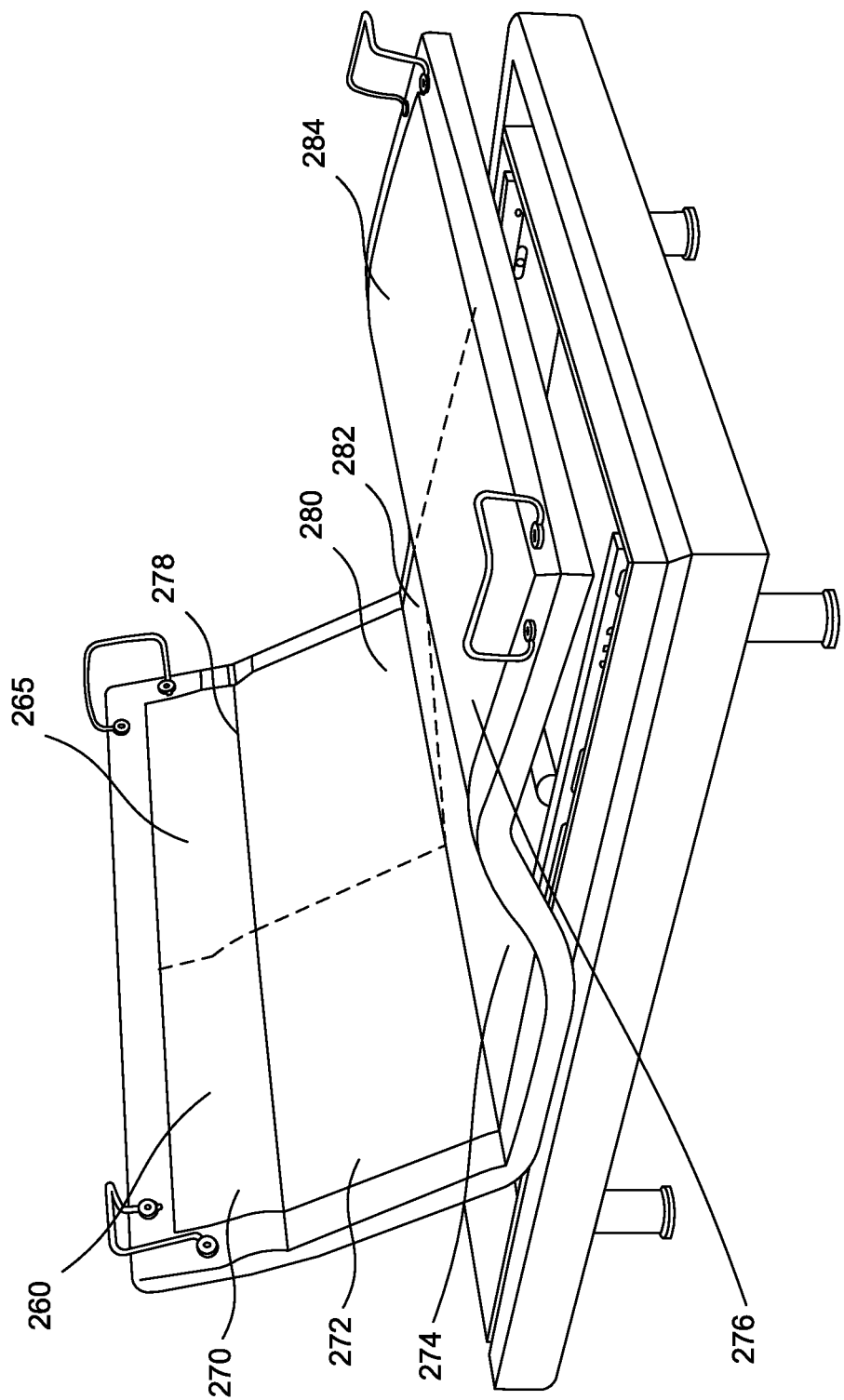
FIG. 2C is an adjustable bed frame including a plurality of zones, according to one embodiment.

FIG. 2C is an adjustable bed frame including a plurality of zones, according to one embodiment. The adjustable bed frame includes a plurality of zones 260, 265 corresponding to a plurality of users. Each includes a plurality of adjustable sections. Zone 260 includes adjustable sections 270-276, and zone 265 includes adjustable sections 278-284. Each adjustable section can be adjusted independently. When the processor 230 detects a user in one of the zones, for example, zone 260, the processor 230 identifies the user based on the breathing rate, heart rate, or motion associated with a user. According to another embodiment, the computer processor receives the user ID associated with the user from a user device associated with the user. Based on the identification, the processor 230 retrieves from the database 180 the user profile. According to the user profile, the processor 230 adjusts the rest position of the zone 260 to match the user-specified rest position. When a sleeping disorder is detected, the processor 230 sends a control signal to adjust the bed frame to match the user-specified position.

Figure 3:
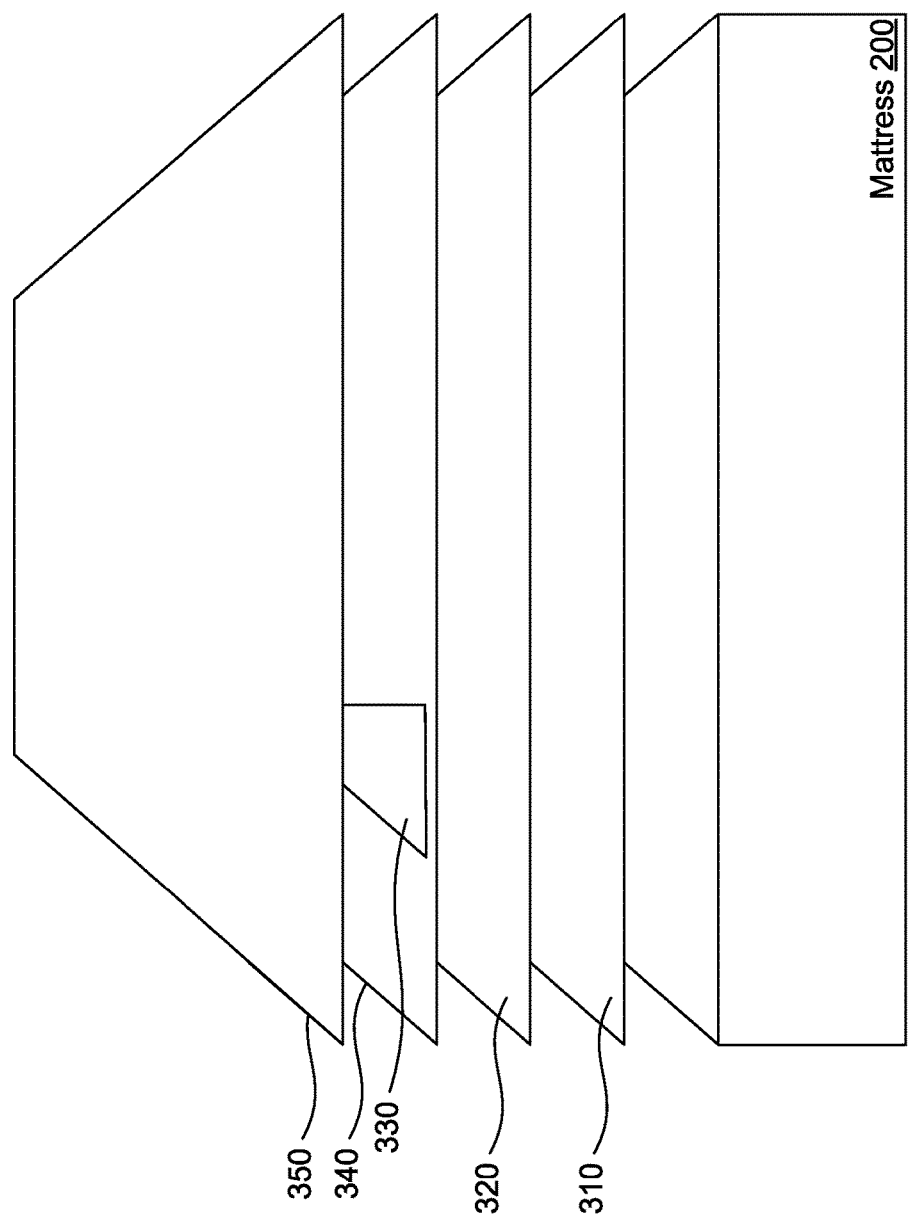
FIG. 3 illustrates an example of layers comprising a bed device, according to one embodiment.

FIG. 3 illustrates an example of layers comprising the bed device of FIG. 1, according to one embodiment. In some embodiments, the bed device 120 is a pad that can be placed on top of the mattress. The pad comprises a number of layers. A top layer 350 comprises fabric. A layer 340 comprises batting and a sensor strip 330. A layer 320 comprises coils for cooling or heating the bed device. A layer 310 comprises waterproof material.

Figure 4A:
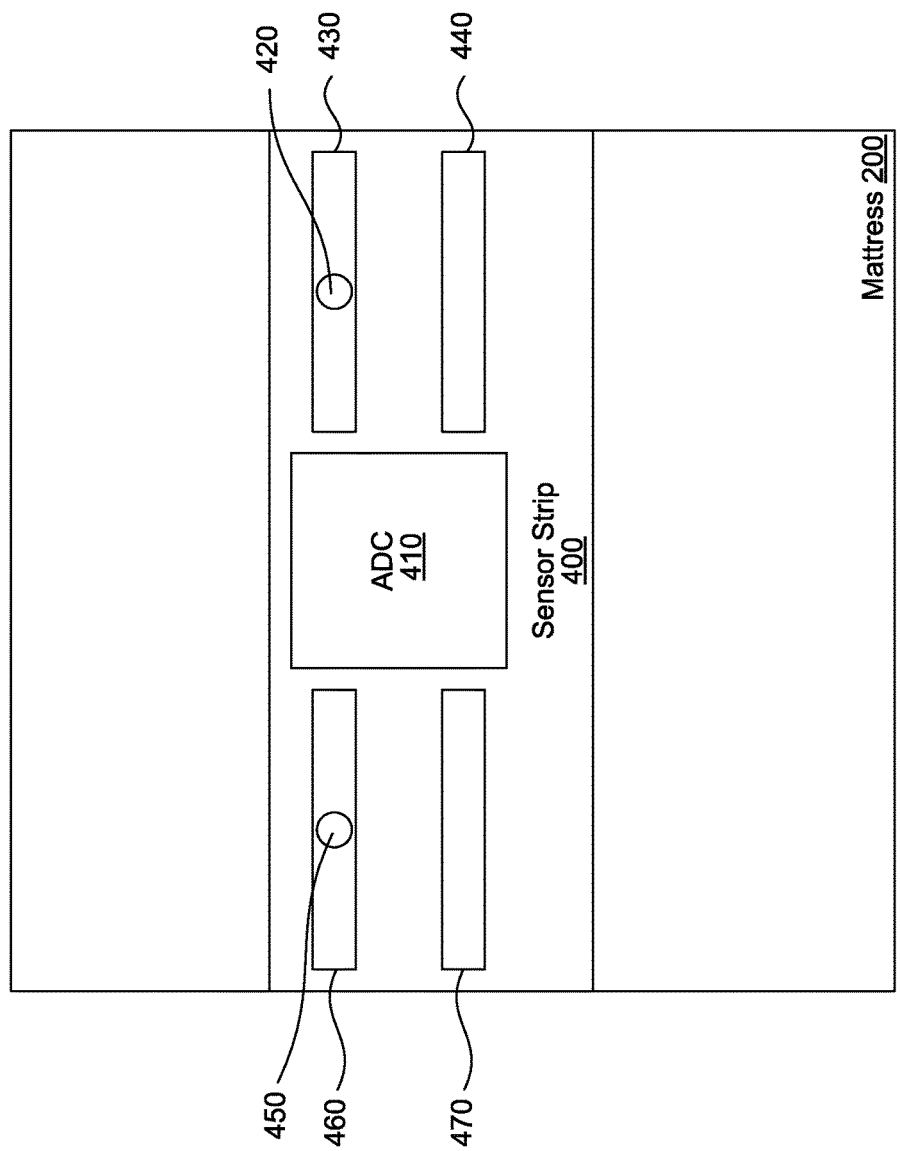
FIG. 4A illustrates a user sensor placed on a sensor strip, according to one embodiment.

FIG. 4A illustrates a user sensor 420, 440, 450, 470 placed on a sensor strip 400, according to one embodiment. In some embodiments, the user sensors 420, 440, 450, 470 can be similar to or part of the sensor strip 210 of FIG. 2. Sensors 470 and 440 comprise a piezo sensor, which can measure a bio signal associated with a user, such as the heart rate and the breathing rate. Sensors 450 and 420 comprise a temperature sensor. According to one embodiment, sensors 450 and 470 measure the bio signals associated with one user, while sensors 420, 440 measure the bio signals associated with another user. Analog-to-digital converter 410 converts the analog sensor signals into digital signals to be communicated to a processor 230. Computer buses 430 and 460, such as the I2C bus, communicate the digitized bio signals to a processor.

Figure 4B:
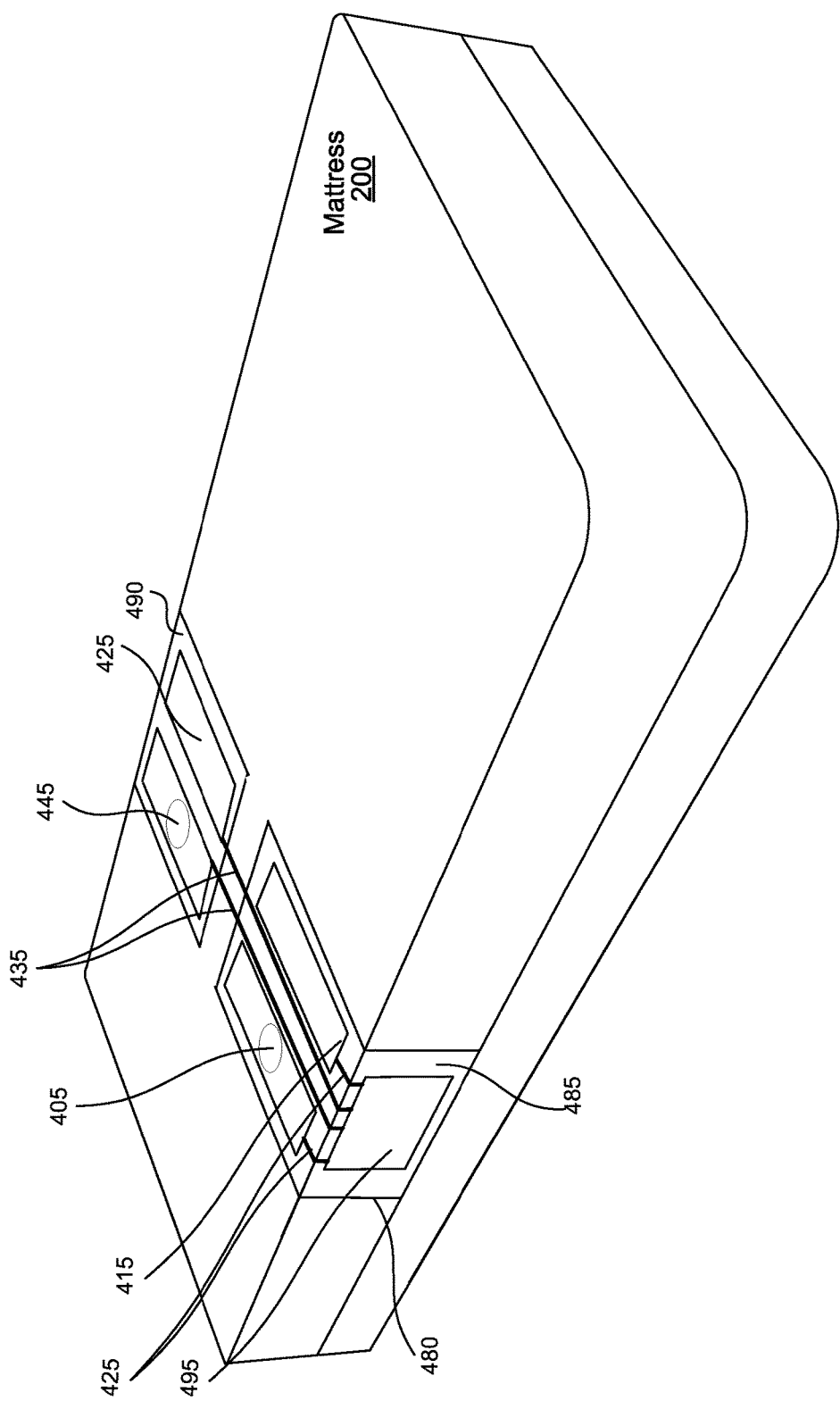
FIG. 4B illustrates a user sensor placed on a sensor strip according to another embodiment.

FIG. 4B illustrates a user sensor placed on a sensor strip according to another embodiment. The sensor strip 480 includes two sections 485, 490. Each sensor strip section 485, 490 includes a temperature sensor 405, 445, respectively, and a piezo sensor 415, 425, respectively. The temperature sensors 405, 445 and the piezo sensors 415, 425 are connected to the analog-to-digital converter 495 using wires 425, 435 respectively. The analog-to-digital converter 495 is placed on the side of the strip. In other embodiments, there can be multiple analog-to-digital converters placed on the strip, where the multiple analog-to-digital converters correspond to each sensor strip section 485, 490. In various embodiments, there can be a plurality of sensors strips 480, 400 associated with the mattress 200.

Figure 5B:
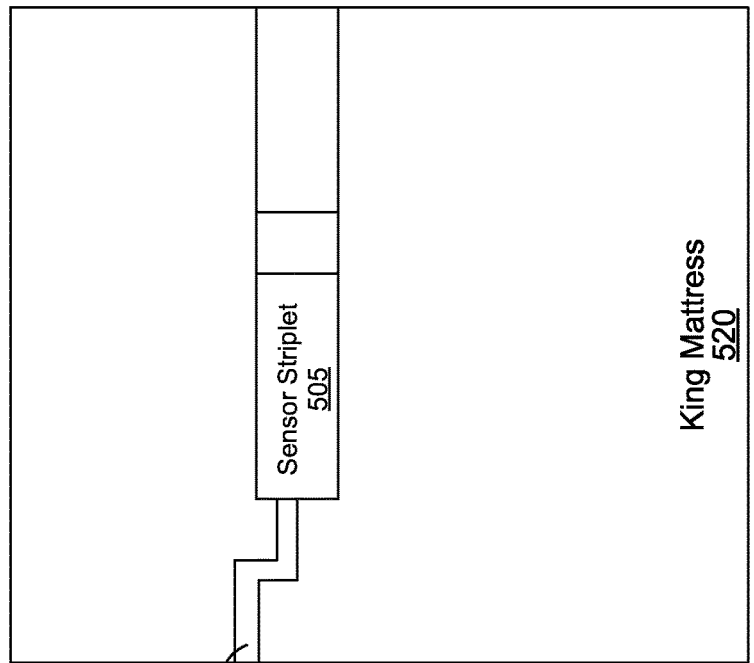
FIGS. 5A, 5B, 5C, and 5D show different configurations of a sensor strip to fit different size mattresses, according to one embodiment.
Figure 5A:
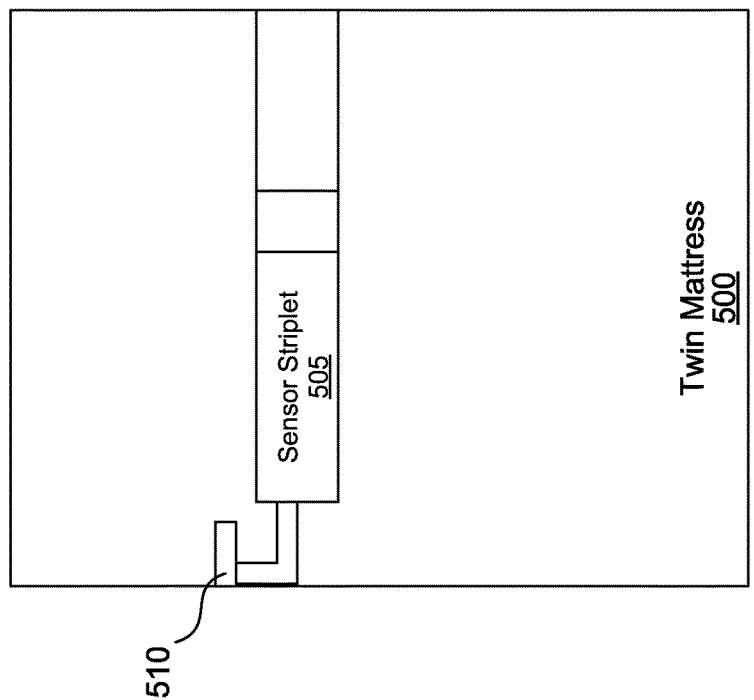
Figure 5C:
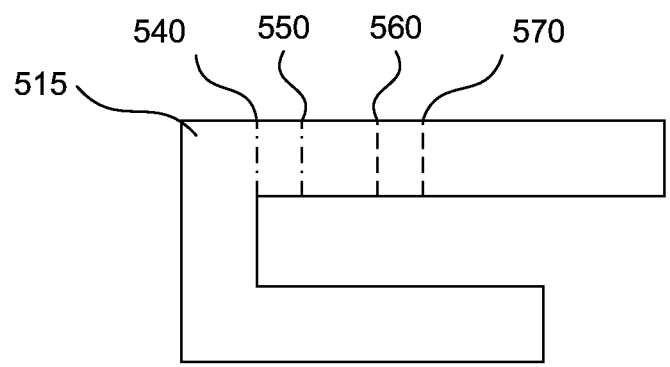
Figure 5D:
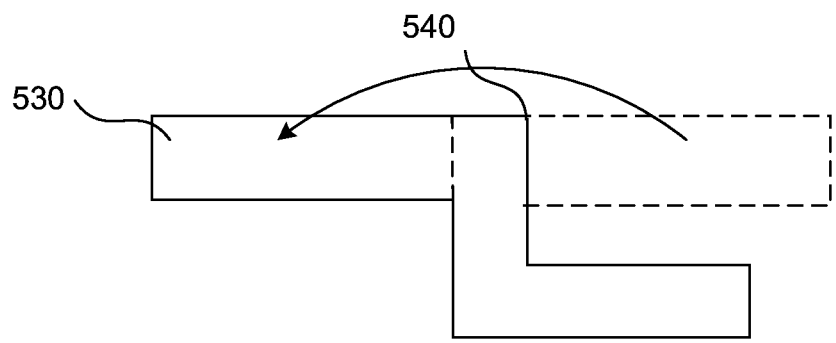

FIGS. 5A and 5B show different configurations of the sensor strip, to fit different size mattresses, according to one embodiment. FIGS. 5C and 5D show how such different configurations of the sensor strip can be achieved. Specifically, sensor strip 400 comprises a computer bus 510, 530, and a sensor striplet 505. The computer bus 510, 530 can be bent at predetermined locations 540, 550, 560, 570. Bending the computer bus 515 at location 540 produces the maximum total length of the computer bus 530. Computer bus 530, combined with a sensor striplet 505, fits a king size mattress 520. Bending the computer bus 515 at location 570 produces the smallest total length of the computer bus 510. Computer bus 510, combined with a sensor striplet 505, fits a twin size mattress 500. Bending the computer bus 515 at location 560 enables the sensor strip 400 to fit a full size bed. Bending the computer bus 515 at location 550 enables the sensor strip 400 to fit a queen size bed. In some embodiments, twin mattress 500 or king mattress 520 can be similar to the mattress 200 of FIG. 2.

Figure 6A:
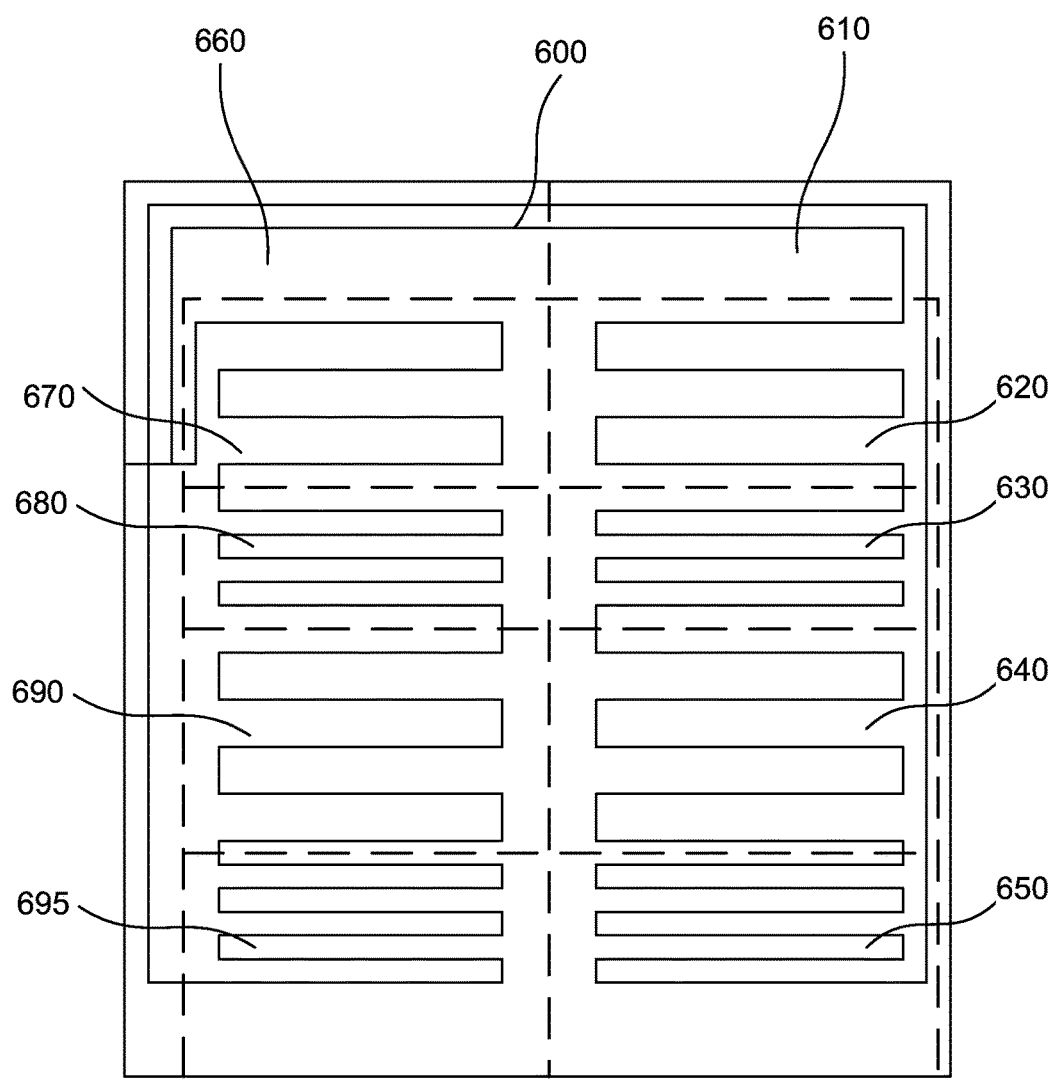
FIG. 6A illustrates the division of the heating coil into zones and subzones, according to one embodiment.

FIG. 6A illustrates the division of the heating coil 600 into zones and subzones, according to one embodiment. Specifically, the heating coil 600 is divided into two zones 660 and 610, each corresponding to one user of the bed. Each zone 660 and 610 can be heated or cooled independently of the other zone in response to the user's needs. To achieve independent heating of the two zones 660 and 610, the power supply associated with the heating coil 600 is divided into two zones, each power supply zone corresponding to a single user zone 660, 610. Further, each zone 660 and 610 is further subdivided into subzones. Zone 660 is divided into subzones 670, 680, 690, and 695. Zone 610 is divided into subzones 620, 630, 640, and 650. The distribution of coils in each subzone is configured so that the subzone is uniformly heated. However, the subzones may differ among themselves in the density of coils. For example, the data associated with the user subzone 670 has lower density of coils than subzone 680. This will result in subzone 670 having lower temperature than subzone 680, when the coils are heated. Similarly, when the coils are used for cooling, subzone 670 will have higher temperature than subzone 680. According to one embodiment, subzones 680 and 630 with highest coil density correspond to the user's lower back; and subzones 695 and 650 with highest coil density correspond to the user's feet.

According to one embodiment, even if the users switch sides of the bed, the system will correctly identify which user is sleeping in which zone by identifying the user based on any of the following signals alone, or in combination: heart rate, breathing rate, body motion, or body temperature associated with the user. The system can also identify the user by receiving from a user device associated with the user an identification (ID) associated with the user. For example, the user can specify the user ID of the person sleeping on the sensor strip. If there are multiple sensor strips and/or multiple sensor, the user can specify the ID of the person associated with each sensor strip and/or each sensor.

In another embodiment, the power supply associated with the heating coil 600 is divided into a plurality of zones, each power supply zone corresponding to a subzone 620, 630, 640, 650, 670, 680, 690, 695. The user can control the temperature of each subzone 620, 630, 640, 650, 670, 680, 690, 695 independently. Further, each user can independently specify the temperature preferences for each of the subzones. Even if the users switch sides of the bed, the system will correctly identify the user, and the preferences associated with the user by identifying the user based on any of the following signals alone, or in combination: heart rate, breathing rate, body motion, or body temperature associated with the user. According to another embodiment, if the users switch sides of the bed, the system receives the user ID of the new user from a user device associated with the user, and retrieves the preferences associated with the user.

Figure 6B:
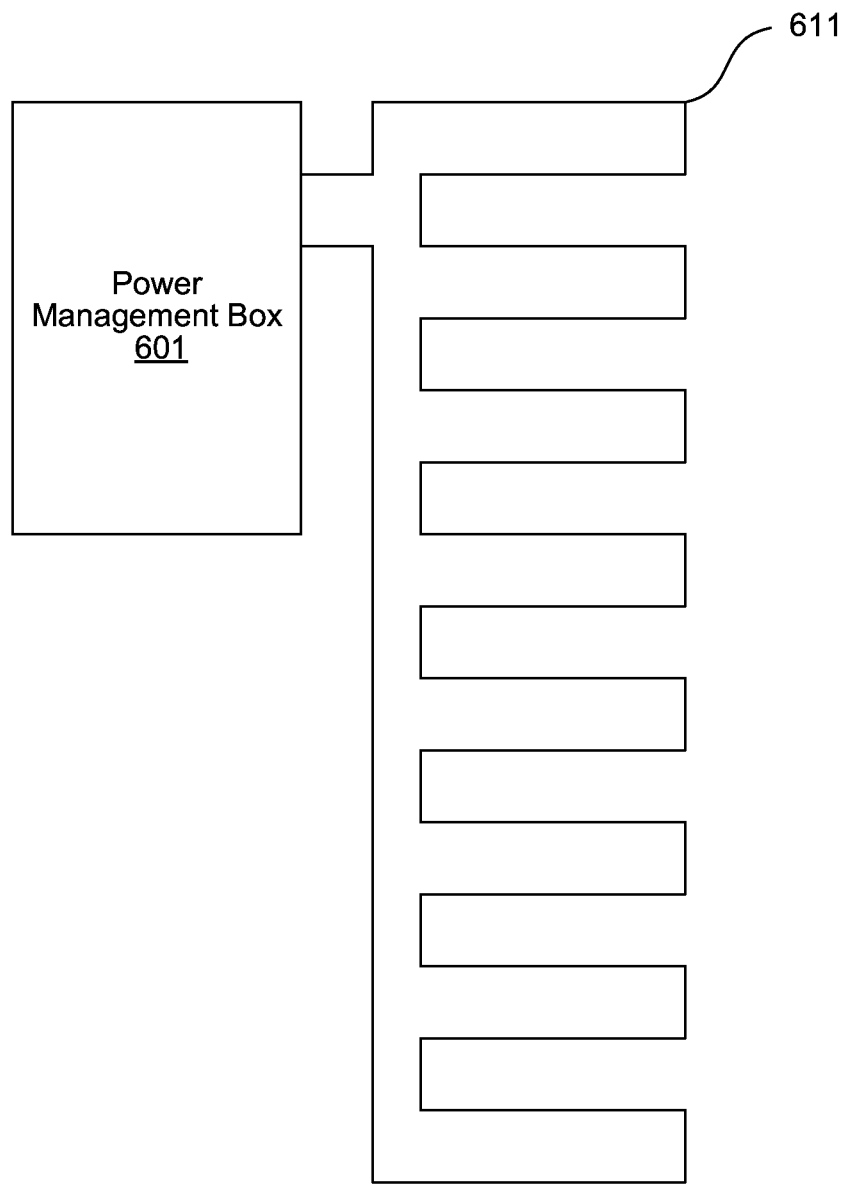
FIGS. 6B and 6C illustrate the independent control of the different subzones, according to one embodiment.
Figure 6C:
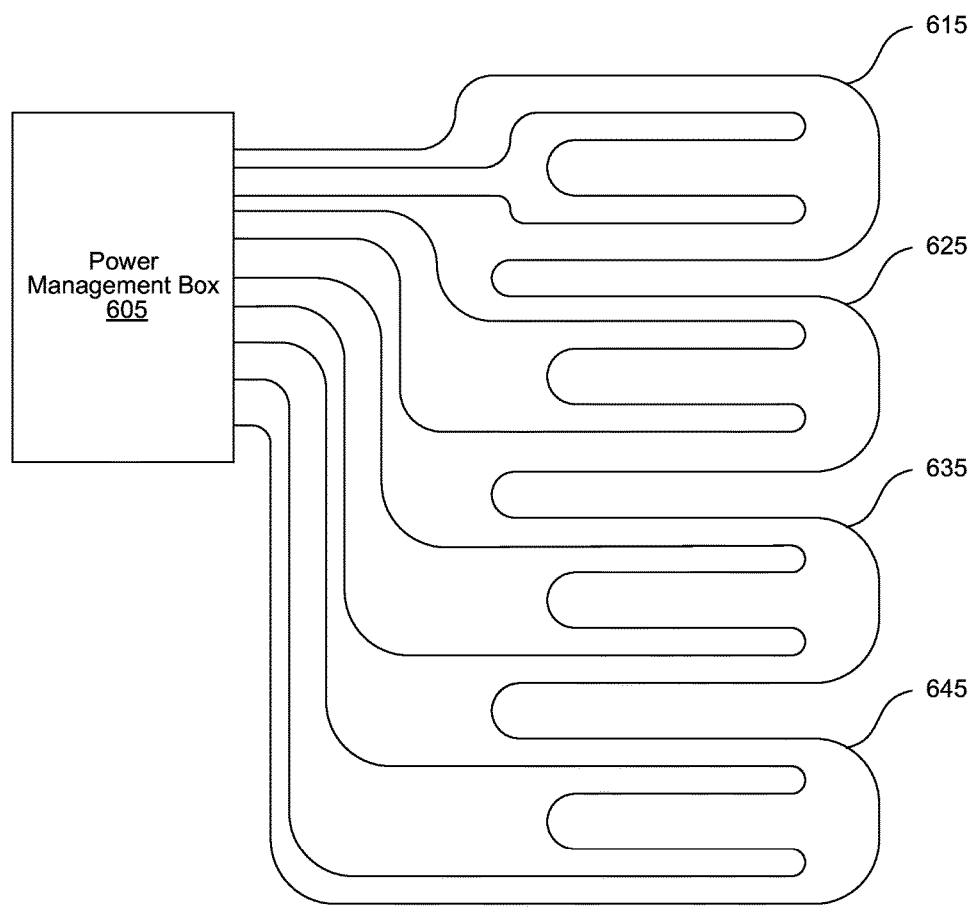

FIGS. 6B and 6C illustrate the independent control of the different subzones in each zone 610, 660, according to one embodiment. A set of uniform coils 611, connected to power management box 601, uniformly heats or cools the bed. Another set of coils, targeting specific areas of the body such as the neck, the back, the legs, or the feet, is layered on top of the uniform coils 611. Subzone 615 heats or cools the neck. Subzone 625 heats or cools the back. Subzone 635 heats or cools the legs, and subzone 645 heats or cools the feet. Power is distributed to the coils via duty cycling of the power supply 605. Contiguous sets of coils can be heated or cooled at different levels by assigning the power supply duty cycle to each set of coils. The user can control the temperature of each subzone independently.

Figure 7:
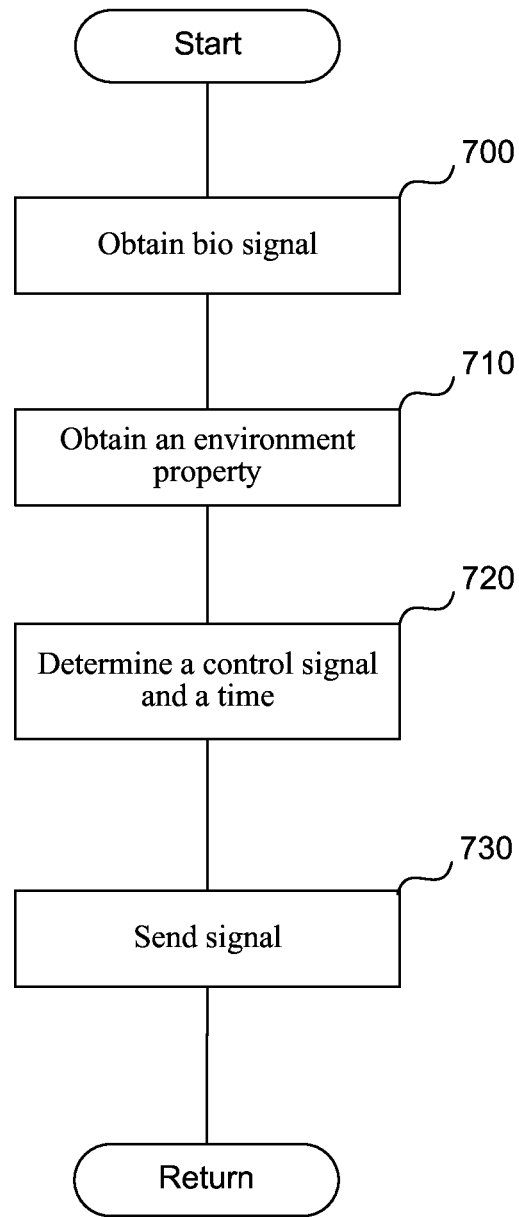
FIG. 7 is a flowchart of the process for deciding when to heat or cool the bed device, according to one embodiment.

FIG. 7 is a flowchart of the process for deciding when to heat or cool the bed device, according to one embodiment. At block 700, the process obtains a biological signal associated with a user, such as presence in bed, motion, breathing rate, heart rate, or a temperature. The process obtains the biological signal from a sensor associated with a user. Further, at block 710, the process obtains one or more environment properties, such as the amount of ambient light and the bed temperature. The process obtains one or more environment properties from an environment sensor associated with the bed device.

At block 720, the process determines the control signal and the time to send a control signal. At block 730, the process sends the control signal to the bed device. For example, if the user is in bed, the bed temperature is low, and the ambient light is low, the process sends a control signal to the bed device. The control signal comprises an instruction to heat the bed device to the average nightly temperature associated with the user. According to another embodiment, the control signal comprises an instruction to heat the bed device to a user-specified temperature. Similarly, if the user is in bed, the bed temperature is high, and the ambient light is low, the process sends a control signal to the bed device to cool the bed device to the average nightly temperature associated with the user. According to another embodiment, the control signal comprises an instruction to cool the bed device to a user-specified temperature.

In another embodiment, in addition to obtaining the biological signal associated with the user, and the environment property, the process obtains a history of biological signals associated with the user. The history of biological signals can be stored in a database associated with the bed device, or in a database associated with a user. The history of biological signals comprises the average bedtime the user went to sleep for each day of the week; that is, the history of biological signals comprises the average bedtime associated with the user on Monday, the average bedtime associated with the user on Tuesday, etc. For a given day of the week, the process determines the average bedtime associated with the user for that day of the week, and sends the control signal to the bed device, allowing enough time for the bed to reach the desired temperature, before the average bedtime associated with the user. The control signal comprises an instruction to heat, or cool the bed to a desired temperature. The desired temperature may be automatically determined, such as by averaging the historical nightly temperature associated with a user, or the desired temperature may be specified by the user.

Bio Signal Processing

The technology disclosed here categorizes the sleep phase associated with a user as light sleep, deep sleep, or REM sleep. Light sleep comprises stage one and stage two sleep. The technology performs the categorization based on the breathing rate associated with the user, heart rate associated with the user, motion associated with the user, and body temperature associated with the user. Generally, when the user is awake the breathing is erratic. When the user is sleeping, the breathing becomes regular. The transition between being awake and sleeping is quick, and lasts less than 1 minute.

Figure 8:
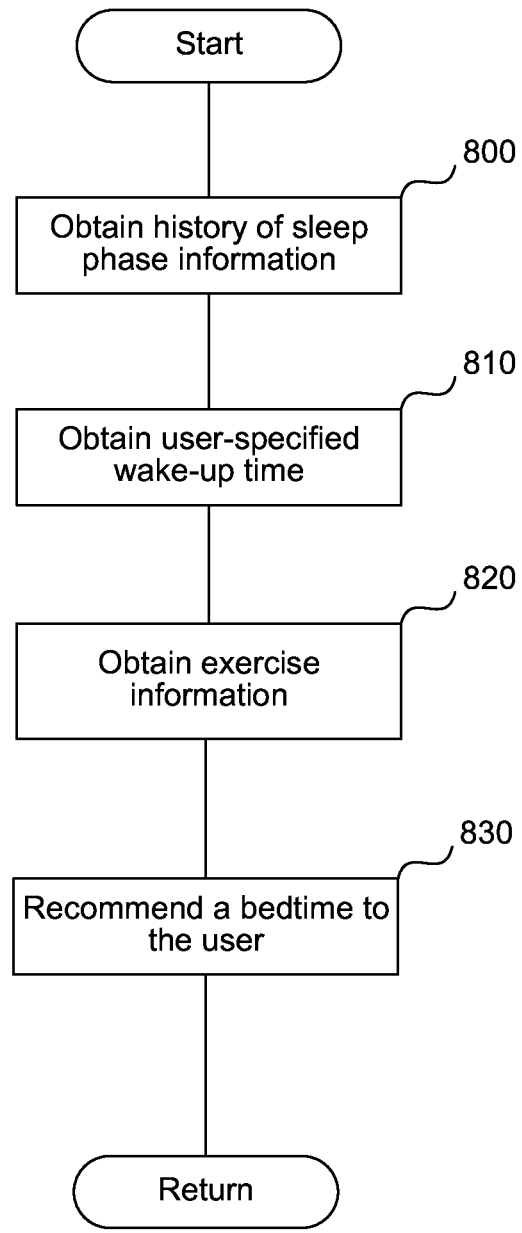
FIG. 8 is a flowchart of the process for recommending a bedtime to the user, according to one embodiment.

FIG. 8 is a flowchart of the process for recommending a bedtime to the user, according to one embodiment. At block 800, the process obtains a history of sleep phase information associated with the user. The history of sleep phase information comprises an amount of time the user spent in each of the sleep phases, light sleep, deep sleep, or REM sleep. The history of sleep phase information can be stored in a database associated with the user. Based on this information, the process determines how much light sleep, deep sleep, and REM sleep, the user needs on average every day. In another embodiment, the history of sleep phase information comprises the average bedtime associated with the user for each day of the week (e.g., the average bedtime associated with the user on Monday, the average bedtime associated with the user on Tuesday, etc.). At block 810, the process obtains user-specified wake-up time, such as the alarm setting associated with the user. At block 820, the process obtains exercise information associated with the user, such as the distance the user ran that day, the amount of time the user exercised in the gym, or the amount of calories the user burned that day. According to one embodiment, the process obtains the exercise information from a user phone, a wearable device, a fitbit bracelet, or a database storing the exercise information. Based on all this information, at block 830, the process recommends a bedtime to the user. For example, if the user has not been getting enough deep and REM sleep in the last few days, the process recommends an earlier bedtime to the user. Also, if the user has exercised more than the average daily exercise, the process recommends an earlier bedtime to the user.

Figure 9:
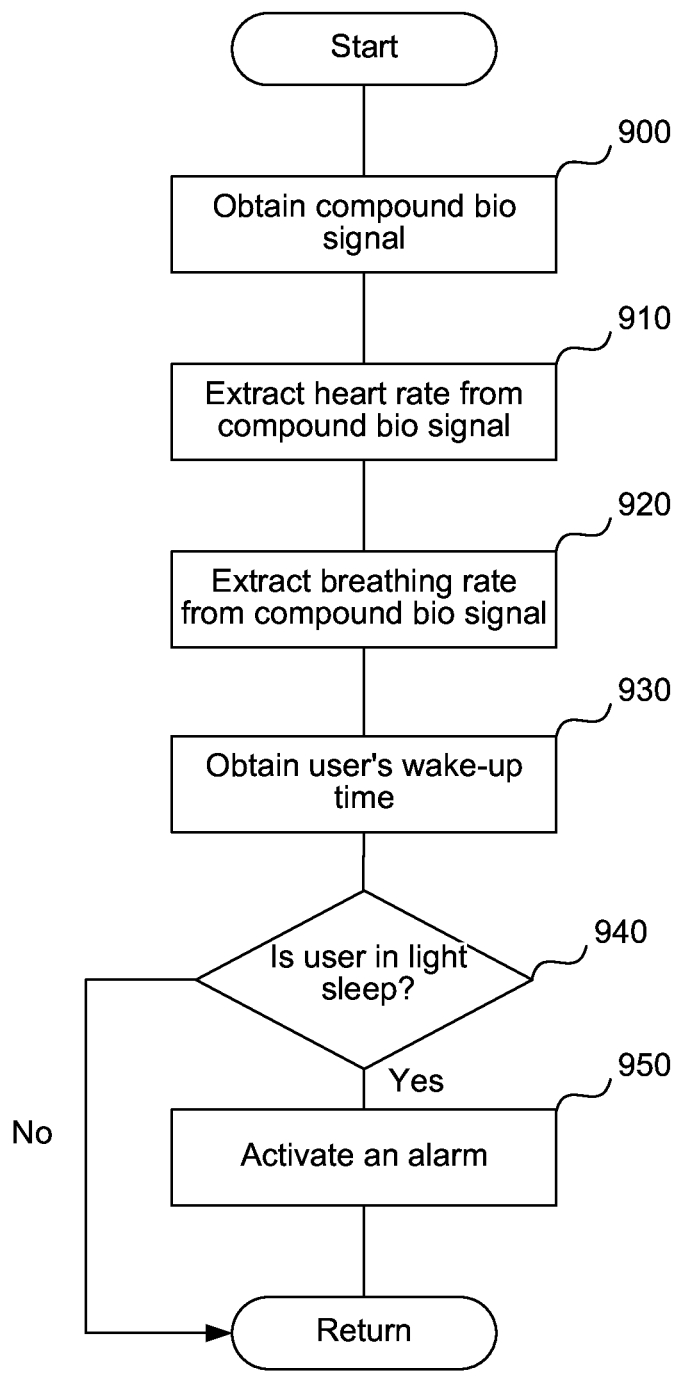
FIG. 9 is a flowchart of the process for activating a user's alarm, according to one embodiment.

FIG. 9 is a flowchart of the process for activating a user's alarm, according to one embodiment. At block 900, the process obtains the compound bio signal associated with the user. The compound bio signal associated with the user comprises the heart rate associated with the user, and the breathing rate associated with the user. According to one embodiment, the process obtains the compound bio signal from a sensor associated with the user. At block 910, the process extracts the heart rate signal from the compound bio signal. For example, the process extracts the heart rate signal associated with the user by performing low-pass filtering on the compound bio signal. Also, at block 920, the process extracts the breathing rate signal from the compound bio signal. For example, the process extracts the breathing rate by performing bandpass filtering on the compound bio signal. The breathing rate signal includes breath duration, pauses between breaths, as well as breaths per minute. At block 930, the process obtains the user's wake-up time, such as the alarm setting associated with the user. Based on the heart rate signal and the breathing rate signal, the process determines the sleep phase associated with the user, and if the user is in light sleep, and current time is at most one hour before the alarm time, at block 940, the process activates an alarm. Waking up the user during the deep sleep or REM sleep is detrimental to the user's health because the user will feel disoriented, groggy, and will suffer from impaired memory. Consequently, at block 950, the process activates an alarm, when the user is in light sleep and when the current time is at most one hour before the user-specified wake-up time.

Figure 10:
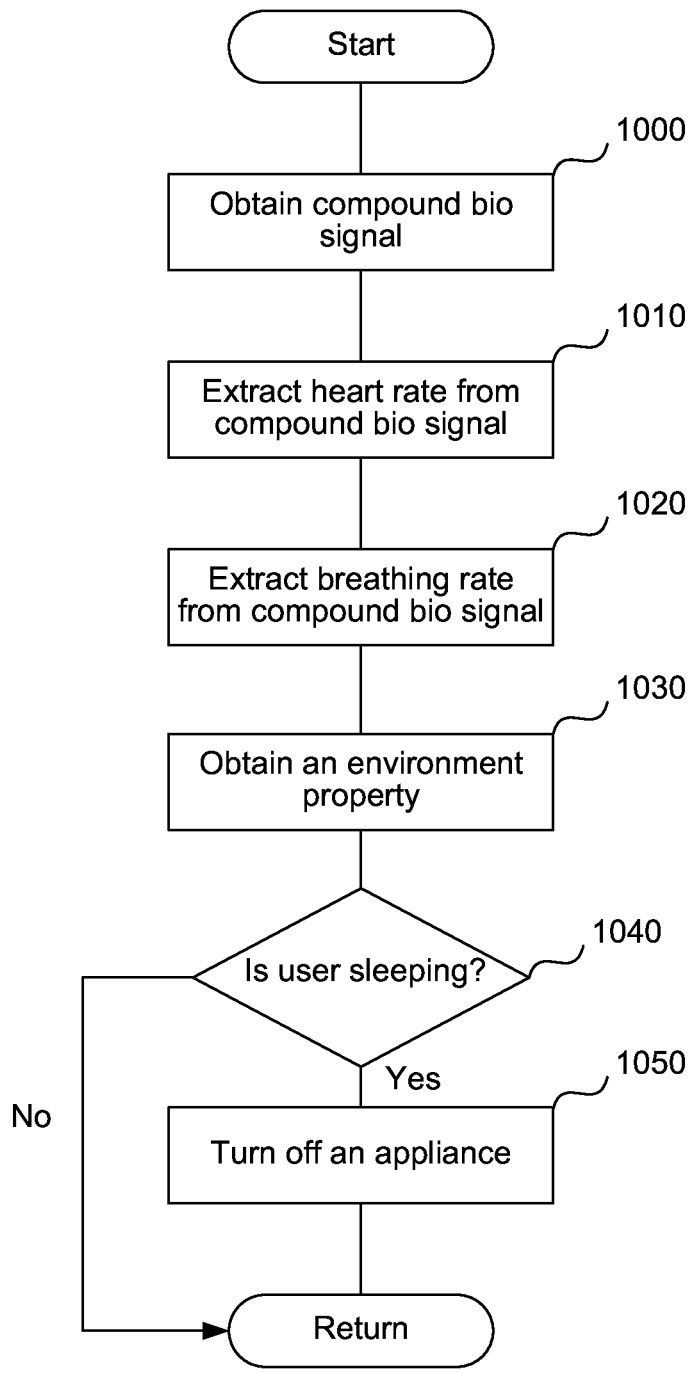
FIG. 10 is a flowchart of the process for turning off an appliance, according to one embodiment.

FIG. 10 is a flowchart of the process for turning off an appliance, according to one embodiment. At block 1000, the process obtains the compound bio signal associated with the user. The compound bio signal comprises the heart rate associated with the user, and the breathing rate associated with the user. According to one embodiment, the process obtains the compound bio signal from a sensor associated with the user. At block 1010, the process extracts the heart rate signal from the compound bio signal by, for example, performing low-pass filtering on the compound bio signal. Also, at block 1020, the process extracts the breathing rate signal from the compound bio signal by, for example, performing bandpass filtering on the compound bio signal. At block 1030, the process obtains an environment property, comprising temperature, humidity, light, or sound from an environment sensor associated with the sensor strip. Based on the environment property and the sleep state associated with the user, at block 1040, the process determines whether the user is sleeping. If the user is sleeping, the process, at block 1050, turns an appliance off. For example, if the user is asleep and the environment temperature is above the average nightly temperature, the process turns off the thermostat. Further, if the user is asleep and the lights are on, the process turns off the lights. Similarly, if the user is asleep and the TV is on, the process turns off the TV.

Smart Home

Figure 11:
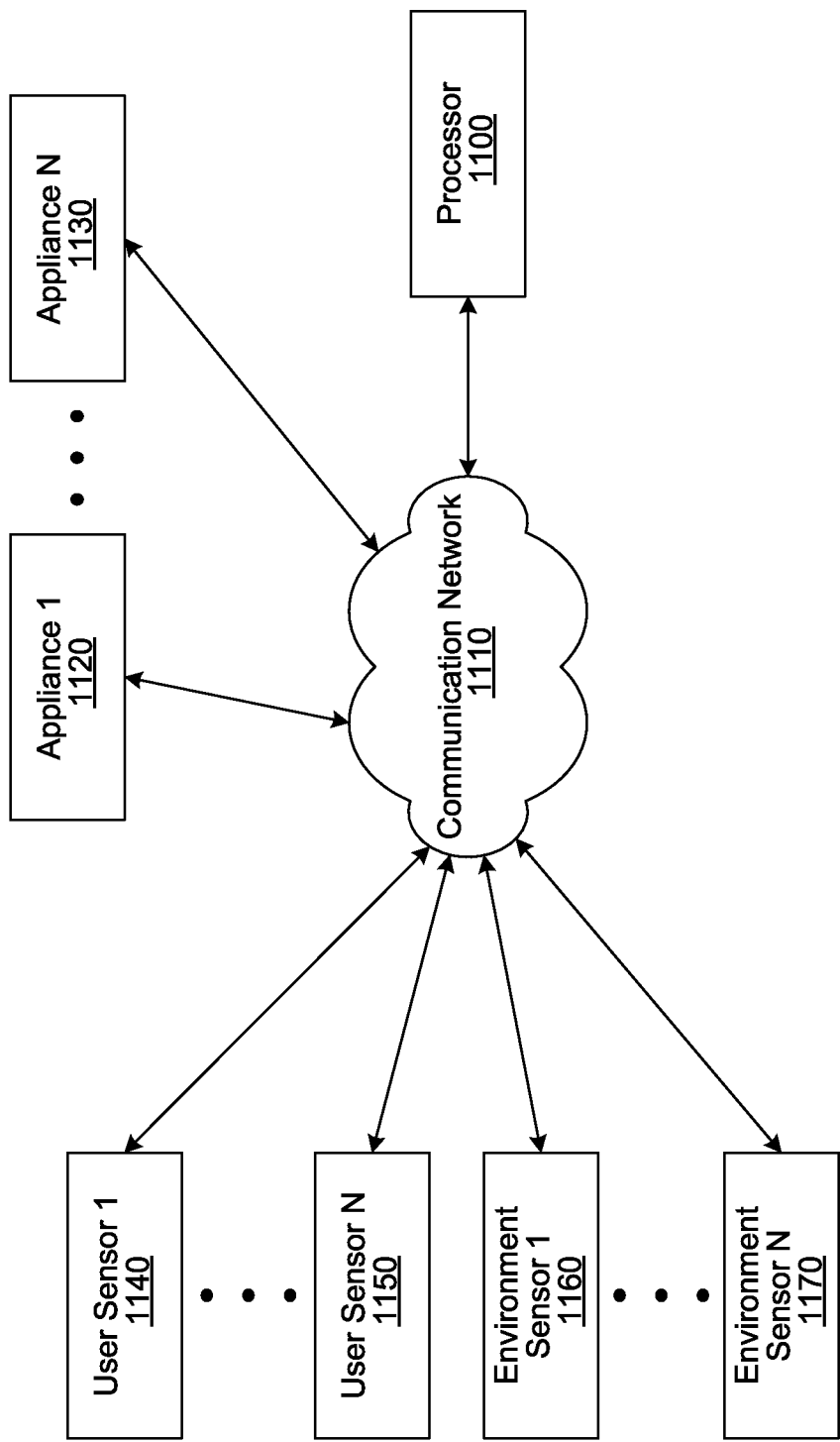
FIG. 11 is a diagram of a system capable of automating the control of the home appliances, according to one embodiment.

FIG. 11 is a diagram of a system capable of automating the control of the home appliances, according to one embodiment. Any number of user sensors 1140, 1150 monitor biological signals associated with the user, such as temperature, motion, presence, heart rate, or breathing rate. Any number of environment sensors 1160, 1170 monitor environment properties, such as temperature, sound, light, or humidity. According to one embodiment, the environment sensors 1160, 1170 are placed next to a bed. The user sensors 1140, 1150 and the environment sensors 1160, 1170 communicate their measurements to the processor 1100. The processor 1100 determines, based on the current biological signals associated with the user, historical biological signals associated with the user, user-specified preferences, exercise data associated with the user, and the environment properties received, a control signal, and a time to send the control signal to an appliance 1120, 1130.

The processor 1100 is any type of microcontroller, or any processor in a mobile terminal, fixed terminal, or portable terminal including a mobile handset, station, unit, device, multimedia computer, multimedia tablet, Internet node, cloud computer, communicator, desktop computer, laptop computer, notebook computer, netbook computer, tablet computer, personal communication system (PCS) device, personal navigation device, personal digital assistants (PDAs), audio/video player, digital camera/camcorder, positioning device, television receiver, radio broadcast receiver, electronic book device, game device, the accessories and peripherals of these devices, or any combination thereof.

The processor 1100 can be connected to the user sensor 1140, 1150, or the environment sensor 1160, 1170 by a computer bus, such as an I2C bus. Also, the processor 1100 can be connected to the user sensor 1140, 1150, or environment sensor 1160, 1170 by a communication network 1110. By way of example, the communication network 1110 connecting the processor 1100 to the user sensor 1140, 1150, or the environment sensor 1160, 1170 includes one or more networks such as a data network, a wireless network, a telephony network, or any combination thereof. The data network may be any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, or any combination thereof. In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, code division multiple access (CDMA), wideband code division multiple access (WCDMA), wireless fidelity (WiFi), wireless LAN (WLAN), Bluetooth®, Internet Protocol (IP) data casting, satellite, mobile ad-hoc network (MANET), and the like, or any combination thereof.

Figure 12:
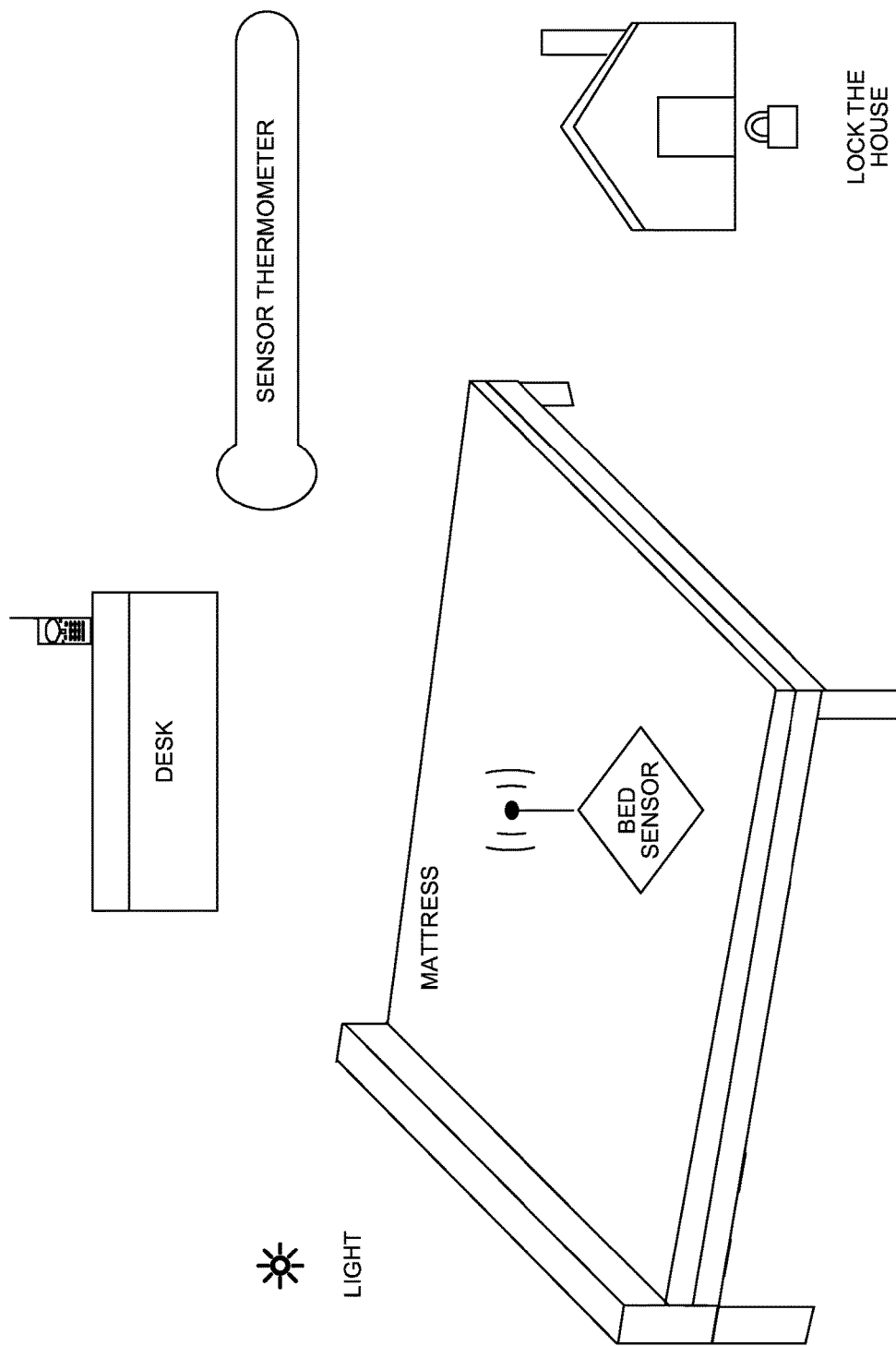
FIG. 12 is an illustration of the system capable of controlling an appliance and a home, according to one embodiment.

FIG. 12 is an illustration of the system capable of controlling an appliance and a home, according to one embodiment. The appliances that the system disclosed here can control, comprise an alarm, a coffee machine, a lock, a thermostat, a bed device, a humidifier, or a light. For example, if the system detects that the user has fallen asleep, the system sends a control signal to the lights to turn off, to the locks to engage, and to the thermostat to lower the temperature. According to another example, if the system detects that the user has woken up and it is morning, the system sends a control signal to the coffee machine to start making coffee.

Figure 13:
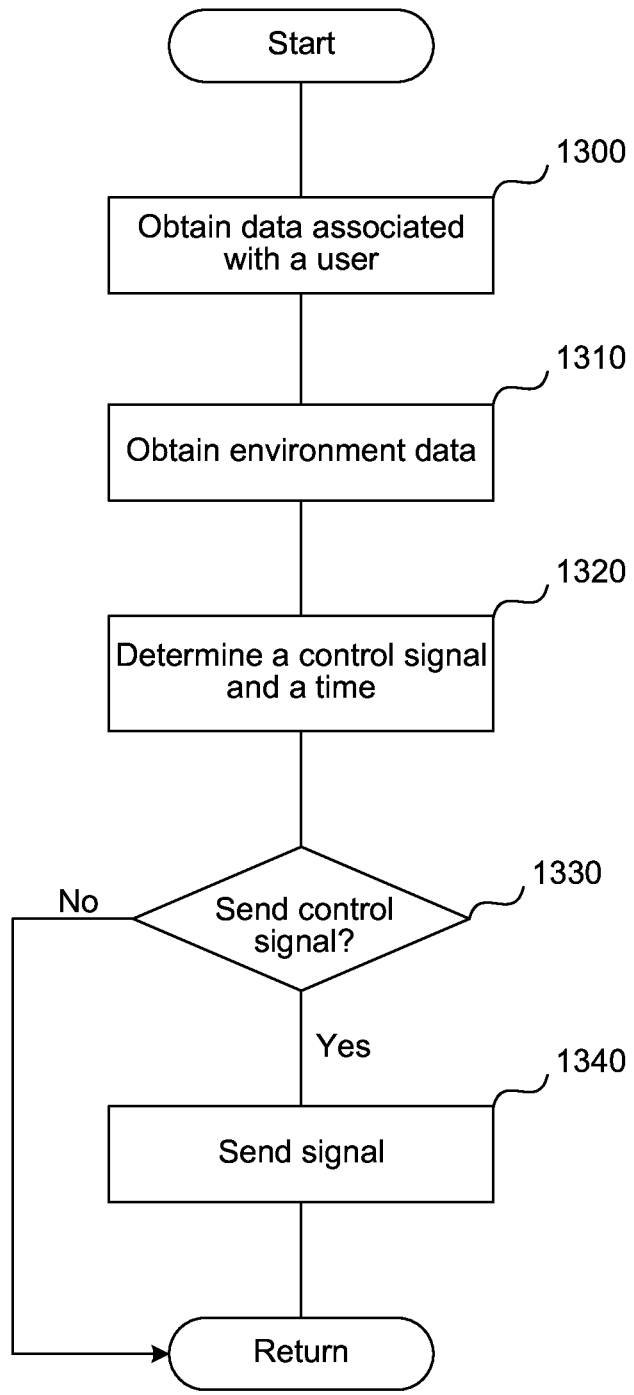
FIG. 13 is a flowchart of the process for controlling an appliance, according to one embodiment.

FIG. 13 is a flowchart of the process for controlling an appliance, according to one embodiment. In one embodiment, at block 1300, the process obtains a history of biological signals, such as at what time the user goes to bed on a particular day of the week (e.g., the average bedtime associated with the user on Monday, the average bedtime associated with the user on Tuesday, etc.). The history of biological signals can be stored in a database associated with the user, or in a database associated with the bed device. In another embodiment, at block 1300, the process also obtains user-specified preferences, such as the preferred bed temperature associated with the user. Based on the history of biological signals and user-specified preferences, the process, at block 1320, determines a control signal, and a time to send the control signal to an appliance. At block 1330, the process determines whether to send a control signal to an appliance. For example, if the current time is within half an hour of the average bedtime associated with the user on that particular day of the week, the process, at block 1340, sends a control signal to an appliance. For example, the control signal comprises an instruction to turn on the bed device, and the user-specified bed temperature. Alternatively, the bed temperature is determined automatically, such as by calculating the average nightly bed temperature associated with a user.

According to another embodiment, at block 1300, the process obtains a current biological signal associated with a user from a sensor associated with the user. At block 1310, the process also obtains environment data, such as the ambient light, from an environment sensor associated with a bed device. Based on the current biological signal, the process identifies whether the user is asleep. If the user is asleep and the lights are on, the process sends an instruction to turn off the lights. In another embodiment, if the user is asleep, the lights are off, and the ambient light is high, the process sends an instruction to the blinds to shut. In another embodiment, if the user is asleep, the process sends an instruction to the locks to engage.

In another embodiment, the process, at block 1300, obtains a history of biological signals, such as at what time the user goes to bed on a particular day of the week (e.g., the average bedtime associated with the user on Monday, the average bedtime associated with the user on Tuesday, etc.). The history of biological signals can be stored in a database associated with the bed device, or in a database associated with a user. Alternatively, the user may specify a bedtime for the user for each day of the week. Further, the process obtains the exercise data associated with the user, such as the number of hours the user spent exercising, or the heart rate associated with the user during exercising. According to one embodiment, the process obtains the exercise data from a user phone, a wearable device, fitbit bracelet, or a database associated with the user. Based on the average bedtime for that day of the week, and the exercise data during the day, the process, at block 1320, determines the expected bedtime associated with the user that night. The process then sends an instruction to the bed device to heat to a desired temperature, before the expected bedtime. The desired temperature can be specified by the user, or can be determined automatically, based on the average nightly temperature associated with the user.

Figure 14:
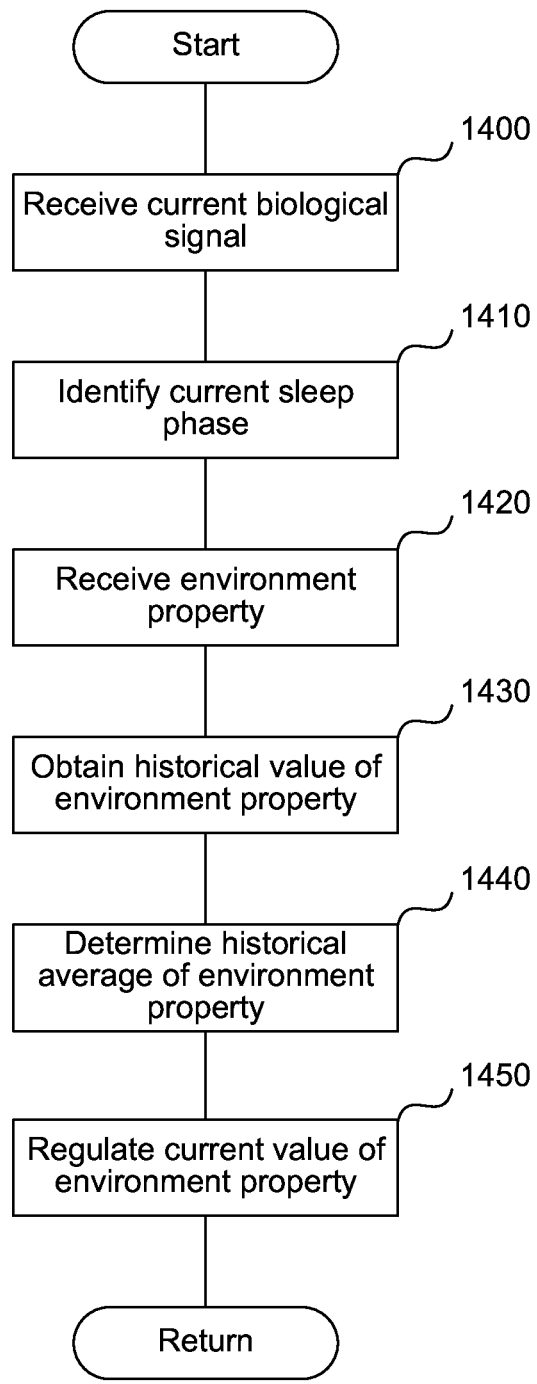
FIG. 14 is a flowchart of the process for controlling an appliance, according to another embodiment.

FIG. 14 is a flowchart of the process for controlling an appliance, according to another embodiment. The process, at block 1400, receives a current biological signal associated with the user, such as the heart rate, breathing rate, presence, motion, or temperature, associated with the user. Based on the current biological signal, the process, at block 1410, identifies current sleep phase, such as light sleep, deep sleep, or REM sleep. The process, at block 1420 also receives a current environment property value, such as the temperature, the humidity, the light, or the sound. The process, at block 1430, accesses a database, which stores historical values associated with the environment property and the current sleep phase. That is, the database associates each sleep phase with an average historical value of the different environment properties. The database may be associated with the bed device, may be associated with the user, or may be associated with a remote server. The process, at block 1440, then calculates a new average of the environment property based on the current value of the environment property and the historical value of the environment property, and assigns the new average to the current sleep phase in the database. If there is a mismatch between the current value of the environment property, and the historical average, the process, at block 1450, regulates the current value to match the historical average. For example, the environment property can be the temperature associated with the bed device. The database stores the average bed temperature corresponding to each of the sleep phases, light sleep, deep sleep, REM sleep. If the current bed temperature is below the historical average, the process sends a control signal to increase the temperature of the bed to match the historical average.

Monitoring of Biological Signals

Biological signals associated with a person, such as a heart rate or a breathing rate, indicate the person's state of health. Changes in the biological signals can indicate an immediate onset of a disease, or a long-term trend that increases the risk of a disease associated with the person. Monitoring the biological signals for such changes can predict the onset of a disease, can enable calling for help when the onset of the disease is immediate, or can provide advice to the person if the person is exposed to a higher risk of the disease in the long-term.

Figure 15:
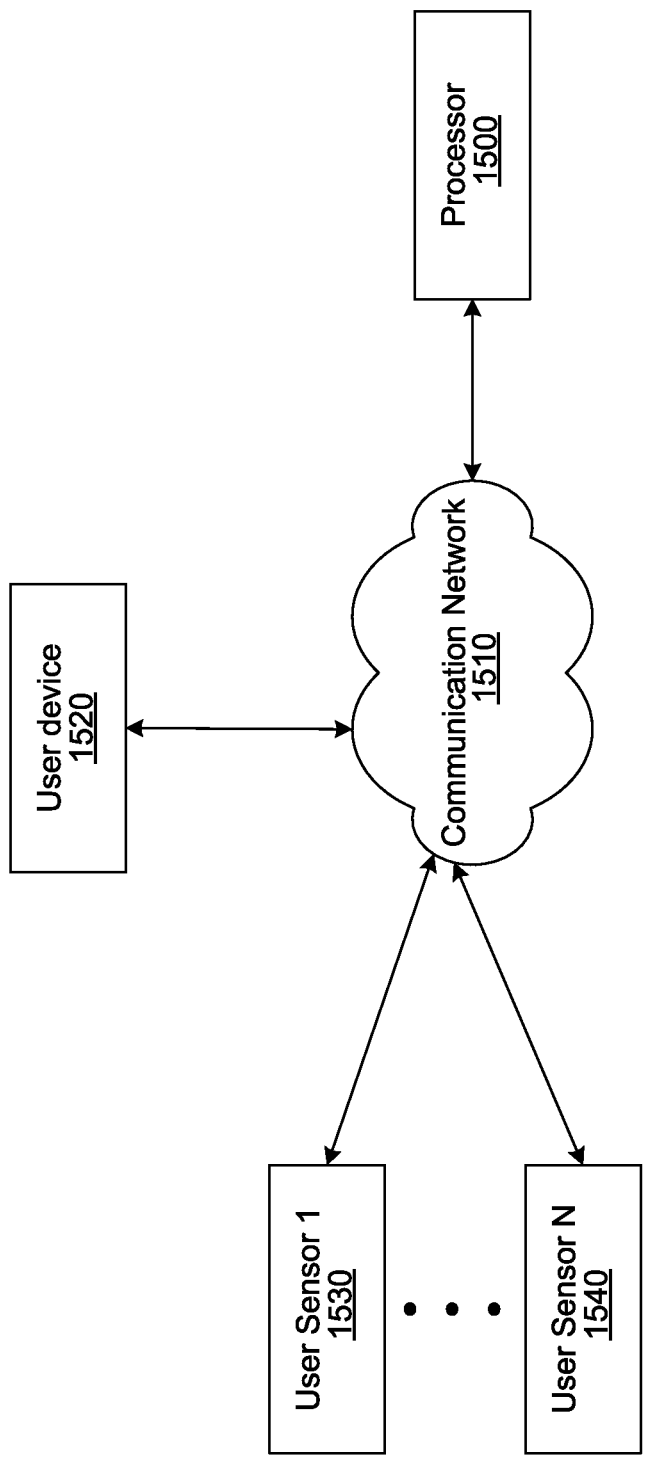
FIG. 15 is a diagram of a system for monitoring biological signals associated with a user, and providing notifications or alarms, according to one embodiment.

FIG. 15 is a diagram of a system for monitoring biological signals associated with a user, and providing notifications or alarms, according to one embodiment. Any number of user sensors 1530, 1540 monitor bio signals associated with the user, such as temperature, motion, presence, heart rate, or breathing rate. The user sensors 1530, 1540 communicate their measurements to the processor 1500. The processor 1500 determines, based on the bio signals associated with the user, historical biological signals associated with the user, or user-specified preferences whether to send a notification or an alarm to a user device 1520. In some embodiments, the user device 1520 and the processor 1500 can be the same device.

The user device 1520 is any type of a mobile terminal, fixed terminal, or portable terminal including a mobile handset, station, unit, device, multimedia computer, multimedia tablet, Internet node, communicator, desktop computer, laptop computer, notebook computer, netbook computer, tablet computer, personal communication system (PCS) device, personal navigation device, personal digital assistants (PDAs), audio/video player, digital camera/camcorder, positioning device, television receiver, radio broadcast receiver, electronic book device, game device, the accessories and peripherals of these devices, or any combination thereof.

The processor 1500 is any type of microcontroller, or any processor in a mobile terminal, fixed terminal, or portable terminal including a mobile handset, station, unit, device, multimedia computer, multimedia tablet, Internet node, cloud computer, communicator, desktop computer, laptop computer, notebook computer, netbook computer, tablet computer, personal communication system (PCS) device, personal navigation device, personal digital assistants (PDAs), audio/video player, digital camera/camcorder, positioning device, television receiver, radio broadcast receiver, electronic book device, game device, the accessories and peripherals of these devices, or any combination thereof.

The processor 1500 can be connected to the user sensor 1530, 1540 by a computer bus, such as an I2C bus. Also, the processor 1500 can be connected to the user sensor 1530, 1540 by a communication network 1510. By way of example, the communication network 1510 connecting the processor 1500 to the user sensor 1530, 1540 includes one or more networks such as a data network, a wireless network, a telephony network, or any combination thereof. The data network may be any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, or any combination thereof. In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, code division multiple access (CDMA), wideband code division multiple access (WCDMA), wireless fidelity (WiFi), wireless LAN (WLAN), Bluetooth®, Internet Protocol (IP) data casting, satellite, mobile ad-hoc network (MANET), and the like, or any combination thereof.

Figure 16:
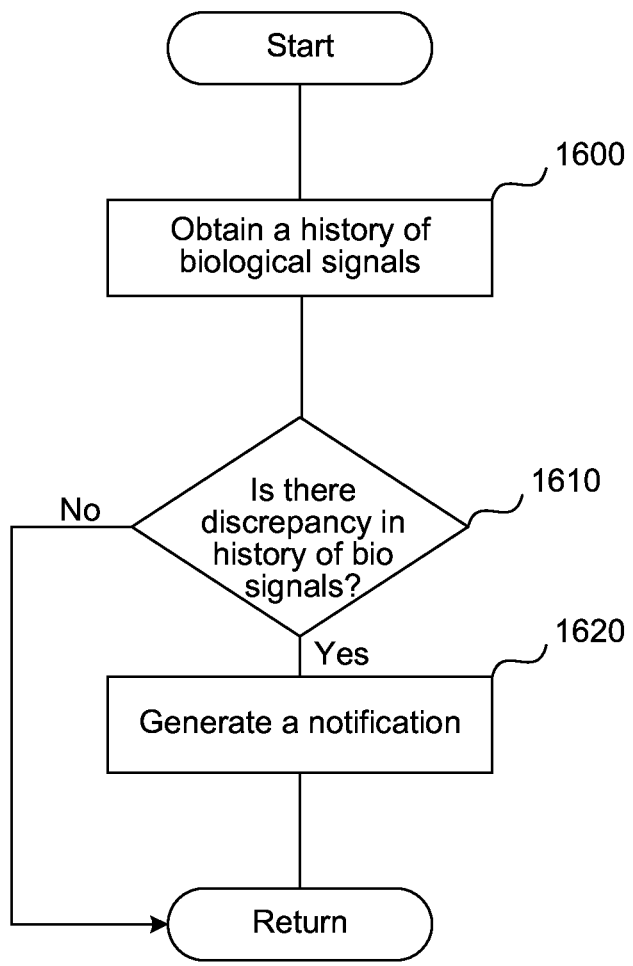
FIG. 16 is a flowchart of a process for generating a notification based on a history of biological signals associated with a user, according to one embodiment.

FIG. 16 is a flowchart of a process for generating a notification based on a history of biological signals associated with a user, according to one embodiment. The process, at block 1600, obtains a history of biological signals, such as the presence history, motion history, breathing rate history, or heart rate history, associated with the user. The history of biological signals can be stored in a database associated with a user. At block 1610, the process determines if there is an irregularity in the history of biological signals within a timeframe. If there is an irregularity, at block 1620, the process generates a notification to the user. The timeframe can be specified by the user, or the timeframe can be automatically determined based on the type of irregularity. For example, the heart rate associated with the user goes up within a one day timeframe when the user is sick. According to one embodiment, the process detects an irregularity, specifically, that a daily heart rate associated with the user is higher than normal. Consequently, the process warns the user that the user may be getting sick. According to another embodiment, the process detects an irregularity, such as that an elderly user is spending at least 10% more time in bed per day over the last several days, than the historical average. The process generates a notification to the elderly user, or to the elderly user's caretaker, such as how much more time the elderly user is spending in bed. In another embodiment, the process detects an irregularity such as an increase in resting heart rate, by more than 15 beats per minute, over a ten-year period. Such an increase in the resting heart rate doubles the likelihood that the user will die from a heart disease, compared to those people whose heart rates remained stable. Consequently, the process warns the user that the user is at risk of a heart disease.

Figure 17:
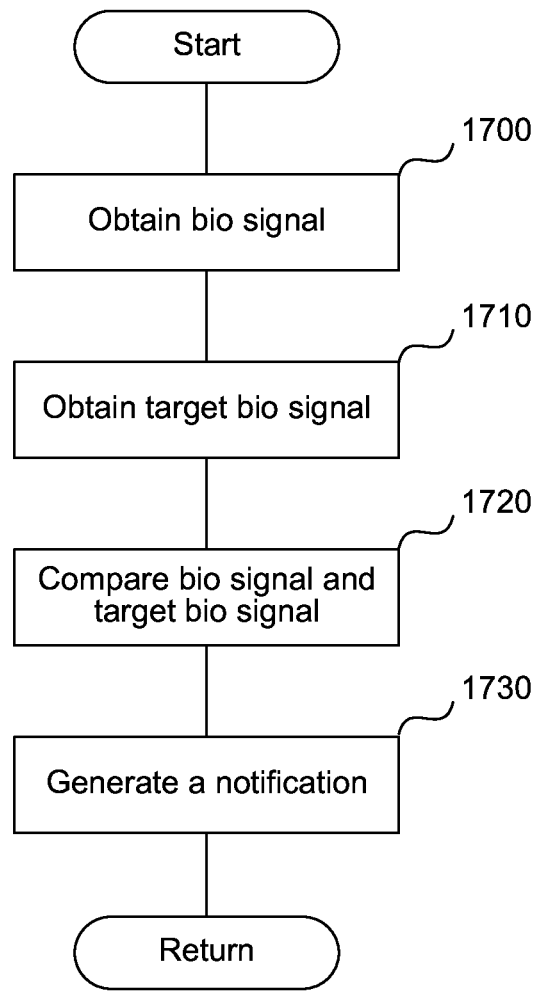
FIG. 17 is a flowchart of a process for generating a comparison between a biological signal associated with a user and a target biological signal, according to one embodiment.

FIG. 17 is a flowchart of a process for generating a comparison between a biological signal associated with a user and a target biological signal, according to one embodiment. The process, at block 1700, obtains a current biological signal associated with a user, such as presence, motion, breathing rate, temperature, or heart rate, associated with the user. The process obtains the current biological signal from a sensor associated with the user. The process, at block 1710, then obtains a target biological signal, such as a user-specified biological signal, a biological signal associated with a healthy user, or a biological signal associated with an athlete. According to one embodiment, the process obtains the target biological signal from a user, or a database storing biological signals. The process, at block 1720, compares the current bio signal associated with the user and the target bio signal, and generates a notification based on the comparison at block 1730. The comparison of the current bio signal associated with the user and the target bio signal comprises detecting a higher frequency in the current biological signal then in the target biological signal, detecting a lower frequency in the current biological signal than in the target biological signal, detecting higher amplitude in the current biological signal than in the target biological signal, or detecting lower amplitude in the current biological signal than in the target biological signal.

According to one embodiment, the process of FIG. 17 can be used to detect if an infant has a higher risk of sudden infant death syndrome ("SIDS"). In SIDS victims less than one month of age, heart rate is higher than in healthy infants of the same age, during all sleep phases. SIDS victims greater than one month of age show higher heart rates during the REM sleep phase. In the case of monitoring an infant for a risk of SIDS, the process obtains the current bio signal associated with the sleeping infant, and a target biological signal associated with the heart rate of a healthy infant, where the heart rate is at the high end of a healthy heart rate spectrum. The process obtains the current bio signal from a sensor strip associated with the sleeping infant. The process obtains the target biological signal from a database of biological signals. If the frequency of the biological signal of the infant exceeds the target biological signal, the process generates a notification to the infant's caretaker, that the infant is at higher risk of SIDS.

According to another embodiment, the process of FIG. 17 can be used in fitness training. A normal resting heart rate for adults ranges from 60 to 100 beats per minute. Generally, a lower heart rate at rest implies more efficient heart function and better cardiovascular fitness. For example, a well-trained athlete might have a normal resting heart rate closer to 40 beats per minute. Thus, a user may specify a target rest heart rate of 40 beats per minute. The process of FIG. 17 generates a comparison between the actual bio signal associated with the user and the target bio signal at block 1720, and based on the comparison, the process generates a notification whether the user has reached his target, or whether the user needs to exercise more, at block 1730.

Figure 18:
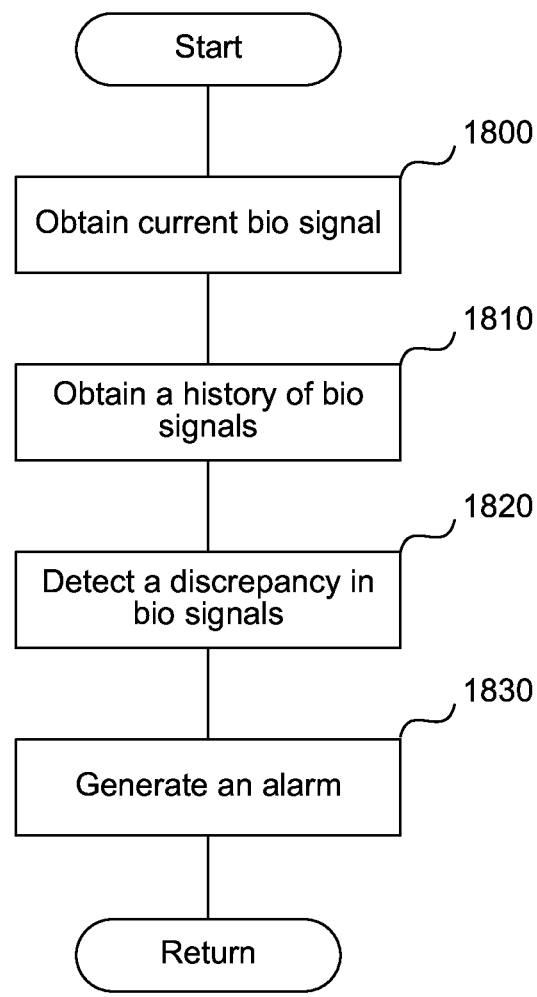
FIG. 18 is a flowchart of a process for detecting the onset of a disease, according to one embodiment.

FIG. 18 is a flowchart of a process for detecting the onset of a disease, according to one embodiment. The process, at block 1800, obtains the current bio signal associated with a user, such as presence, motion, temperature, breathing rate, or heart rate, associated with the user. The process obtains the current bio signal from a sensor associated with the user. Further, the process, at block 1810, obtains a history of bio signals associated with the user from a database. The history of bio signals comprises the bio signals associated with the user, accumulated over time. The history of biological signals can be stored in a database associated with a user. The process, at block 1820, then detects a discrepancy between the current bio signal and the history of bio signals, where the discrepancy is indicative of an onset of a disease. The process, at block 1830, then generates an alarm to the user's caretaker. The discrepancy between the current bio signal and the history of bio signals comprises a higher frequency in the current bio signal than in the history of bio signals, or a lower frequency in the current bio signal than in the history of bio signals.

According to one embodiment, the process of FIG. 18 can be used to detect an onset of an epileptic seizure. A healthy person has a normal heart rate between 60 and 100 beats per minute. During epileptic seizures, the median heart rate associated with the person exceeds 100 beats per minute.

The process of FIG. 18 detects that the heart rate associated with the user exceeds the normal heart rate range associated with the user. The process then generates an alarm to the user's caretaker that the user is having an epileptic seizure. Although rare, epileptic seizures can cause the median heart rate associated with a person to drop below 40 beats per minute. Similarly, the process of FIG. 18 detects if the current heart rate is below the normal heart rate range associated with the user. The process then generates an alarm to the user's caretaker that the user is having an epileptic seizure.

Snoring and Sleep Apnea Detection

Figure 19:
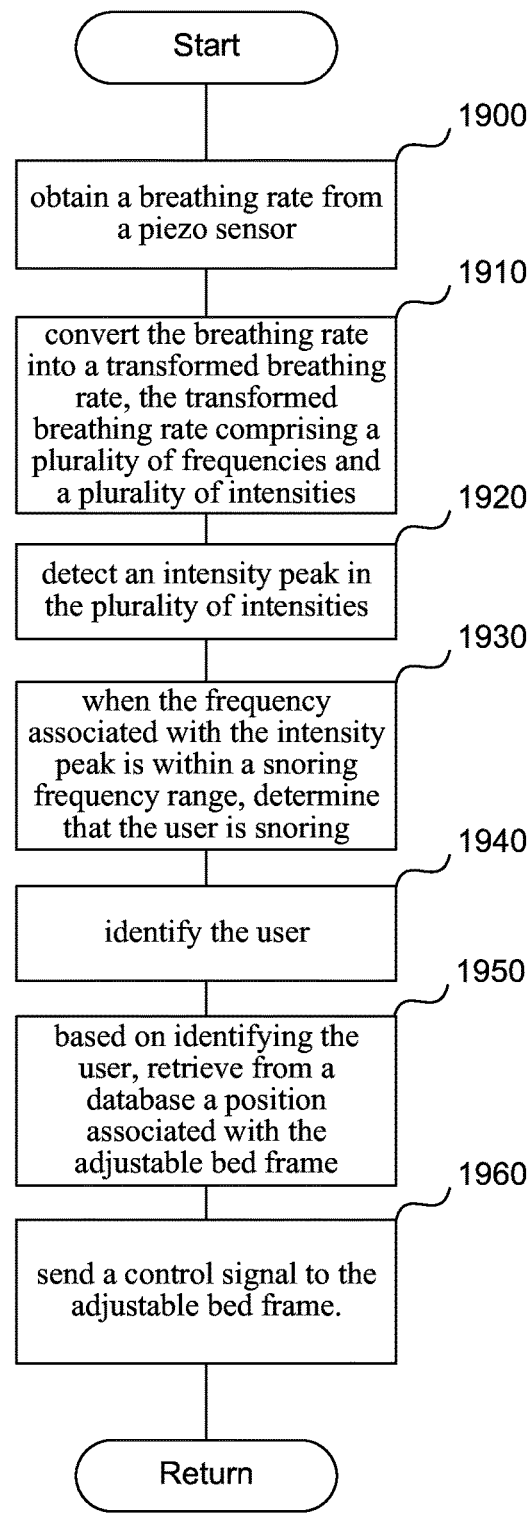
FIG. 19 is a flowchart of a method to detect when a user is snoring, and to position an adjustable bed frame to prevent snoring, according to one embodiment.

FIG. 19 is a flowchart of a method to detect when a user is snoring, and to position an adjustable bed frame to prevent snoring, according to one embodiment. In step 1900, a processor obtains a breathing rate from a piezo sensor. First, the processor receives a compound biological signal from the piezo sensor, where the compound biological signal includes the breathing rate and a heart rate. Then, the processor performs a bandpass filtering operation on the compound biological signal to obtain the breathing rate.

In step 1910, the processor converts the breathing rate into a transformed breathing rate. The transformed breathing rate includes a plurality of frequencies and a plurality of intensities associated with the plurality of frequencies. The processor can perform the conversion using a Fourier Transform, Fast Fourier Transform, or Discrete Fourier Transform.

Breathing rate comprises an inhale portion and an exhale portion. In one embodiment, the processor detects an exhale portion of the breathing rate, and removes the exhale portion from the breathing rate to obtain an inhale breathing rate. The processor then converts the inhale breathing rate into the transformed breathing rate. The processor can perform the conversion using a Fourier Transform, Fast Fourier Transform, or Discrete Fourier Transform.

In step 1920, the processor detects an intensity peak in the plurality of intensities. The intensity peak is a local maximum intensity of the transformed breathing rate. The intensity peak is associated with a frequency in the plurality of frequencies.

In step 1930, the processor determines that the user is snoring when the frequency associated with the intensity peak is within a snoring frequency range. The snoring frequency range includes frequencies within 0 Hz to 150 Hz.

In step 1940, once the processor determines that the user is snoring, the processor identifies the user based on at least one of: the heart rate associated with the user, or the breathing rate associated with the user. In another embodiment, the processor identifies the user by receiving a user ID from a device associated with the user.

In step 1950, once the processor identifies the user, the processor retrieves from a database a position associated with the adjustable bed frame, and the position associated with the identified user, the position configured to prevent snoring. The position can be specified by the user, or can be determined by the system as described herein.

In step 1960, once the processor retrieves the position from the database, the processor sends a control signal to the adjustable bed frame. The control signal includes the position associated with the adjustable bed frame, and can also include an identification (ID) associated with an adjustable section of the adjustable bed frame. The position can correspond to an adjustable section associated with the adjustable bed frame, or the position can correspond to the whole adjustable bed frame, such as when all the adjustable sections of the adjustable bed frame assume the same position.

Figure 20:
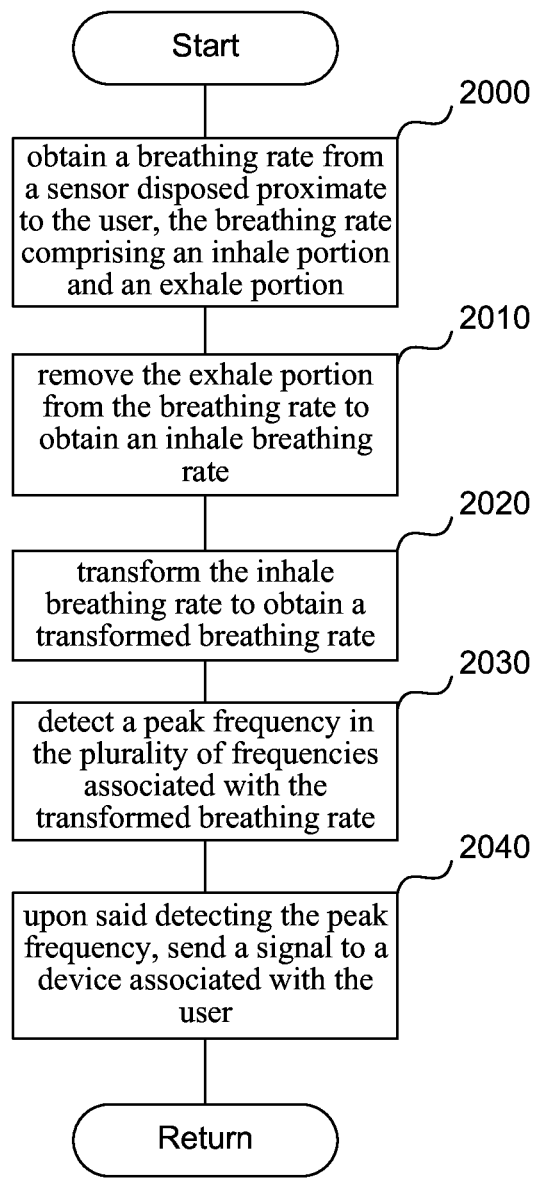
FIG. 20 is a flowchart of a method to detect when a user is experiencing a sleeping disorder, such as snoring and/or sleep apnea, according to one embodiment.

FIG. 20 is a flowchart of a method to detect when a user is experiencing a sleeping disorder, such as snoring and/or sleep apnea, according to one embodiment. In step 2000, the processor obtains a breathing rate from a sensor disposed proximate to the user. The breathing rate includes an inhale portion and an exhale portion. The sensor can be a piezo sensor, and/or a microphone. The piezo sensor and/or the microphone can be disposed within a mattress, a bed pad, a pillow, bed sheets, and/or covers, etc. The microphone can be disposed within the power supply box.

According to one embodiment, the processor obtains the breathing rate by receiving a compound biological signal from a piezo sensor. The compound biological signal includes a heart rate and the breathing rate. The processor then performs a bandpass filter on the compound biological signal to obtain the breathing rate.

According to another embodiment, the processor obtains the breathing rate by receiving a signal from the microphone. The signal includes a sound level in decibels (dB) over time.

In step 2010, the processor removes the exhale portion from the breathing rate to obtain an inhale breathing rate.

In step 2020, the processor transforms the inhale breathing rate to obtain a transformed breathing rate comprising a plurality of frequencies and a plurality of intensities associated with the plurality of frequencies. The processor can perform the transform using Fourier Transform, Fast Fourier Transform, or Discrete Fourier Transform.

In step 2030, the processor detects a peak frequency in the plurality of frequencies associated with the transformed breathing rate, wherein the peak frequency is indicative of the sleeping disorder, such as snoring and/or sleep apnea.

According to one embodiment, the processor detects the peak frequency by finding an intensity peak in the plurality of intensities. The intensity peak is associated with the peak frequency. When the peak frequency associated with the intensity peak is within a sleeping disorder frequency range, the processor determines that the peak frequency is indicative of the sleeping disorder. The snoring and/or sleep apnea frequency range includes frequencies within 0 Hz to 150 Hz.

According to another embodiment, the processor detects the peak frequency by smoothing the transformed breathing rate to obtain a smooth transformed breathing rate. The smooth transformed breathing rate includes a plurality of smooth frequencies, and a plurality of smooth intensities associated with the plurality of smooth frequencies. The smoothing can be done by removing peak frequencies whose formant bandwidths are less than 1 Hz. Various other methods for smoothing the transformed breathing rate can be performed such as cepstral windowing or linear prediction.

After smoothing the transformed breathing rate signal, the processor detects an intensity peak in the plurality of smooth intensities. When the peak frequency associated with the intensity peak is within a sleeping disorder frequency range, the processor determines whether the peak frequency is indicative of sleeping disorder, such as sleep apnea and/or snoring. The sleeping disorder, such as sleep apnea and/or snoring, frequency range includes frequencies within 0 Hz to 150 Hz.

In step 2040, once the processor detects the peak frequency, the processor sends a signal to a device associated with the user. The signal includes an indication that the user is experiencing the sleeping disorder. The processor can analyze breathing rate from the piezo sensor and from the microphone separately, or simultaneously. According to one embodiment, if at least one signal includes an indication that the user is experiencing the sleeping disorder the processor sends the signal to the device associated with the user.

According to one embodiment, in addition, the processor determines a number of snoring and/or sleep apnea episodes by identifying a time period without the sleeping disorder. In other words, once the processor identifies the occurrence of the sleeping disorder, if the processor identifies the time period in the breathing rate which lasts at least 1 minute, and where that time period is without snoring and/or sleep apnea, the processor increments the number of snoring and/or sleep apnea episodes. When the user awakes, the processor sends a notification to the user device, where the notification includes the number of snoring and/or sleep apnea episodes.

According to another embodiment, once the processor detects snoring and/or sleep apnea, the processor sends a notification to a mobile device associated with the user that the user has been snoring and/or has been having sleep apnea episodes.

The processor can also cause the user device to display a graph of the number of snoring and/or sleep apnea episodes over a specified period of time, such as over the last several days, months, years, etc. The graph can also include an average number of snoring and/or sleep apnea episodes for each day of the week.

In one embodiment, the processor sends the signal to an adjustable bed frame. The adjustable bed frame includes a plurality of adjustable sections. The signal includes an identification associated with the adjustable section, and a position associated with said adjustable section, the position configured to prevent snoring and/or sleep apnea. For example, once the processor detects snoring and/or sleep apnea, the processor sends a signal to the adjustable bed frame to raise the adjustable section corresponding to the user's head.

Figure 21:
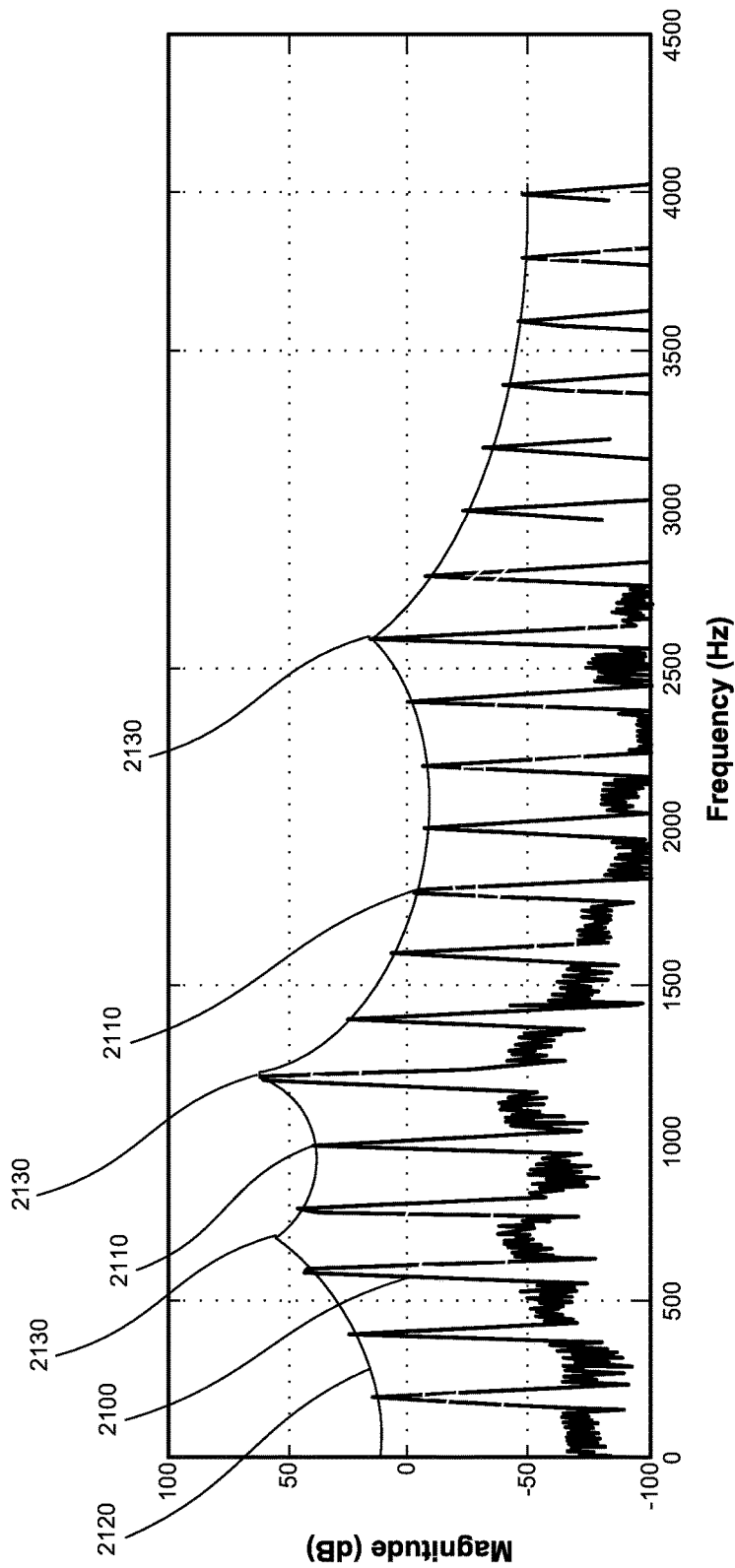
FIG. 21 shows a transformed breathing rate in frequency domain, according to one embodiment.

FIG. 21 shows a transformed breathing rate in frequency domain, according to one embodiment. Graph 2100 is the transformed breathing rate in the frequency domain versus the intensity in decibels (dB). Graph 2100 has a plurality of intensity peaks 2110 (only a few of the intensity peaks are labeled in the figure, for brevity). When the processor does not perform any smoothing of the transformed breathing rate, the processor detects each of the intensity peaks 2110. Graph 2120 is the smooth transformed breathing rate obtained after the processor smoothes the breathing rate. Graph 2120 has a plurality of intensity peaks 2130.

Figure 22:
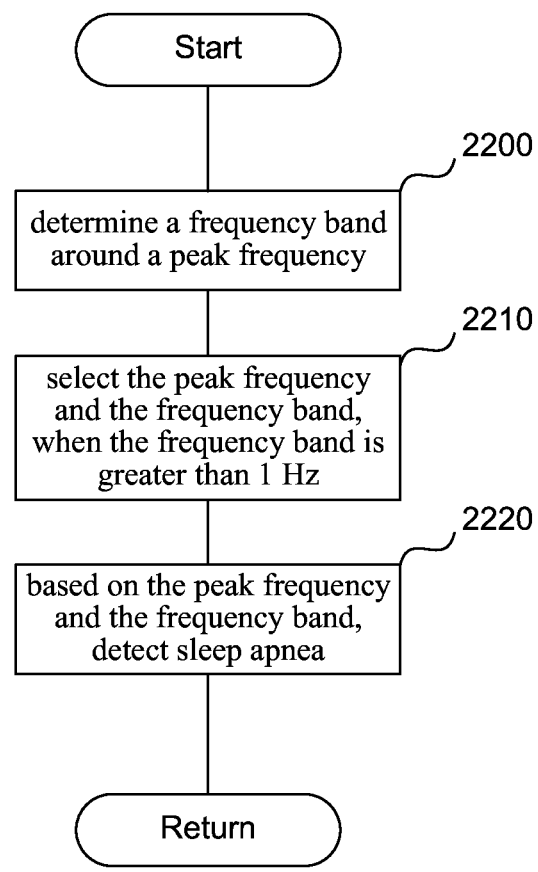
FIG. 22 is a flowchart of a method to detect sleep apnea, according to one embodiment.

FIG. 22 is a flowchart of a method to detect sleep apnea, according to one embodiment. In step 2200, the processor determines a frequency band around the peak frequency. The frequency band is a continuous frequency region around the peak frequency. The frequencies in the frequency band have intensities which differ less than 3 dB from the intensity associated with the peak frequency.

In step 2210, the processor selects the peak frequency and the frequency band, when the frequency band is greater than 1 Hz.

In step 2220, the processor detects sleep apnea based on the peak frequency in the frequency band. According to one embodiment, the processor detects sleep apnea when the peak frequency is within a sleep apnea frequency range and when the frequency band is greater than 20 Hz. The sleep apnea frequency range comprises 0 Hz to 150 Hz.

According to another embodiment, the processor detects sleep apnea when the peak frequency is within a sleep apnea frequency range, wherein the sleep apnea frequency range comprises 0 Hz to 150 Hz.

Figure 23:
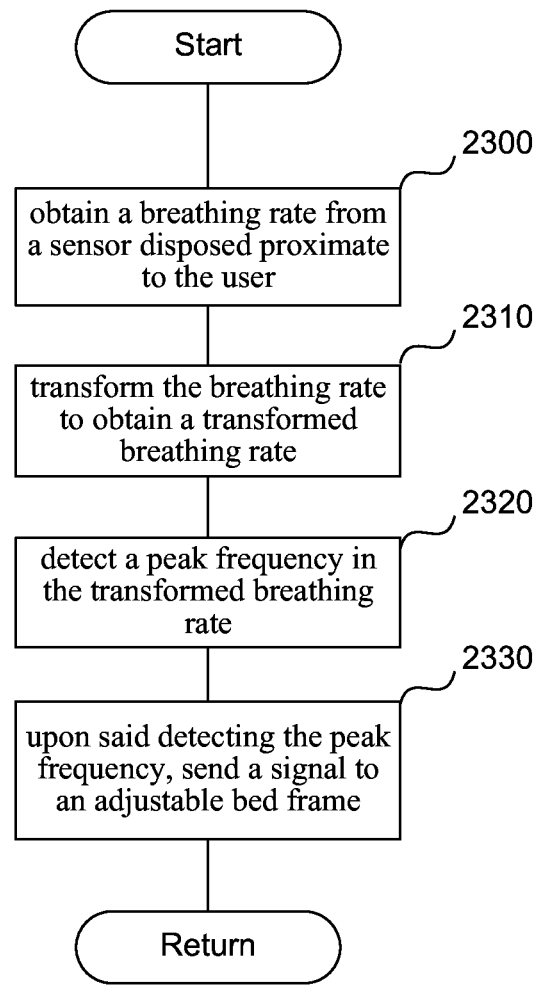
FIG. 23 is a flowchart of a method to adjust an adjustable bed frame upon detecting that a user is experiencing a sleeping disorder, such as snoring and/or sleep apnea, according to one embodiment.

FIG. 23 is a flowchart of a method to adjust an adjustable bed frame upon detecting that a user is experiencing a sleeping disorder, such as snoring and/or sleep apnea, according to one embodiment. In step 2300, the processor obtains a breathing rate from a sensor disposed proximate to the user, the breathing rate comprising an inhale portion and an exhale portion. The sensor can be a piezo sensor, and/or a microphone. The piezo sensor and/or the microphone can be disposed within a mattress, a bed pad, a pillow, bed sheets, and/or covers, etc. The microphone can be disposed within the power supply box.

In step 2310, the processor transforms the breathing rate to obtain a transformed breathing rate comprising a plurality of frequencies and a plurality of intensities associated with the plurality of frequencies. The processor performs the transform using Fourier Transform, Fast Fourier Transform, or Discrete Fourier Transform.

According to one embodiment, before the processor transforms the breathing rate to obtain the transformed breathing rate, the processor first removes the exhale portion from the breathing rate to obtain an inhale breathing rate. The processor than transforms the inhale breathing rate using Fourier Transform, Fast Fourier Transform, or Discrete Fourier Transform.

In step 2320, the processor detects a peak frequency in the transformed breathing rate, wherein the peak frequency is indicative of snoring and/or sleep apnea. According to one embodiment, the processor detects the peak frequency by finding an intensity peak in the plurality of intensities. The intensity peak is associated with the peak frequency. When the peak frequency associated with the intensity peak is within a snoring and/or sleep apnea frequency range, the processor determines that the peak frequency is indicative of snoring and/or sleep apnea. The snoring and/or sleep apnea frequency range includes frequencies within 0 Hz to 150 Hz.

According to another embodiment, the processor detects the peak frequency by smoothing the transformed breathing rate to obtain a smooth transformed breathing rate. The smooth transformed breathing rate comprising a plurality of smooth frequencies, and a plurality of smooth intensities associated with the plurality of smooth frequencies. The processor smoothes the transformed breathing rate by deleting all peak frequencies whose formant bandwidth is less than 1 Hz. Various other methods for smoothing the transformed breathing rate can be performed such as any kind of a method to compute to a spectral envelope.

After smoothing the transformed breathing rate signal, the processor detects an intensity peak in the plurality of smooth intensities. When the peak frequency associated with the intensity peak is within a snoring and/or sleep apnea frequency range, the processor determines that the peak frequency is indicative of a sleeping disorder. The snoring and/or sleep apnea frequency range includes frequencies within 0 Hz to 150 Hz.

In step 2330, once the processor detects the peak frequency, the processor sends a signal to the adjustable bed frame. The signal includes an ID associated with the adjustable bed frame section, a position associated with the adjustable bed frame section, where the position is configured to prevent snoring and/or sleep apnea. Once the adjustable bed frame receives the signal, the adjustable bed frame moves the adjustable section corresponding to the ID, to the specified position.

According to one embodiment, the position can be specified by the user. The processor receives from a user device associated with the user an identification (ID) of an adjustable section associated with the adjustable bed frame, and a preferred position associated with the adjustable section. The signal can include the ID of the adjustable section, and the preferred position of the adjustable section, as specified by the user. For example, the adjustable section can correspond to the head, and the preferred position can be a position elevated from the neutral position.

According to another embodiment, the processor automatically determines the adjustable bed frame position to prevent snoring and/or sleep apnea. Once the processor detects snoring and/or sleep apnea, the processor sends to the adjustable bed frame an ID of an adjustable section associated with the adjustable bed frame, and the position associated with the adjustable section. For example, the processor sends the ID of the head section, and a request to rotate the head section by 10° upward. At least one minute after the adjustable bed frame responds to the signal, the processor detects whether the user is experiencing a sleeping disorder such as snoring and/or sleep apnea. If the user is still experiencing the sleeping disorder, the processor again sends the ID of the head section, and a request to rotate the head section by 10° upward. The processor iteratively adjusts the height of the head section, until the user stops experiencing the sleeping disorder.

Once the processor no longer detects the sleeping disorder, the processor stores the current position of the adjustable bed frame in a database. The processor can in the future retrieve the stored position, and, whenever the sleeping disorder is detected, send the stored position to the adjustable bed frame to prevent snoring and/or sleep apnea.

According to one embodiment, the processor identifies the user based on the breathing rate associated with the user to obtain a user ID. According to another embodiment, the processor receives the user ID from a device associated with the user. Based on the user ID, the processor retrieves from the database a position associated with the adjustable bed frame and with the user ID. The position is configured to prevent snoring and/or sleep apnea, and can be calculated by the processor as described herein, or can be specified by the user as described herein.

Figure 24:
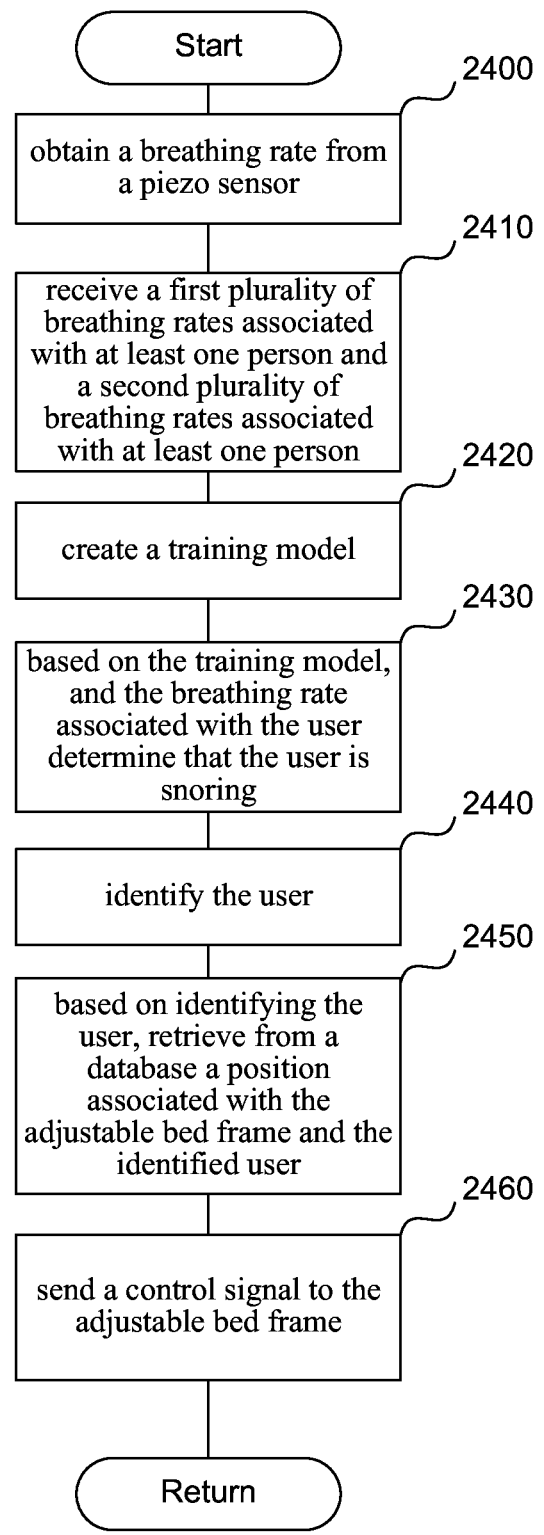
FIG. 24 is a flowchart of a method to detect when a user is experiencing a sleeping disorder, and to position an adjustable bed frame to prevent snoring and/or sleep apnea using machine learning algorithms, according to one embodiment.

FIG. 24 is a flowchart of a method to detect when a user is experiencing a sleeping disorder, and to position an adjustable bed frame to prevent snoring and/or sleep apnea using machine learning algorithms, according to one embodiment. In step 2400, the processor obtains a breathing rate associated with the user from a sensor, such as a piezo sensor and/or a microphone.

In step 2410, the processor receives from a database a first plurality of breathing rates associated with at least one person and a second plurality of breathing rates associated with at least one person. The person can be the user and/or various people whose breathing rates have been measured. Each breathing rate in the first plurality of breathing rates includes normal breathing. Each breathing rate in the second plurality of breathing rates includes breathing indicative of a sleeping disorder such as snoring and/or sleep apnea.

In step 2420, based on the first plurality of breathing rates and the second plurality of breathing rates, the processor creates a training model. The training model is created by providing the first plurality of breathing rates and the second plurality of breathing rates as inputs to create a training model. Creation of the training model can be supervised or unsupervised. In supervised learning, the first plurality of breathing rates provided to the training model can be labeled as normal breathing rates, while the second plurality of breathing rates provided to the training model can be labeled as sleeping disorder breathing rates. In unsupervised learning, the first and second pluralities of breathing rates are unlabeled, and the training model itself determines the categorization.

Creating the training model can include additional steps. In one embodiment, the first and the second plurality of breathing rates are preprocessed before providing inputs to create the training model. Each breathing rate includes an inhale portion and an exhale portion. The exhale portion in each of the breathing rates in the first and the second plurality of breathing rates is removed to obtain a first plurality of inhale breathing rates, and a second plurality of inhale breathing rates. The first plurality of inhale breathing rates and the second plurality of inhale breathing rates are then used as inputs to create the training model.

In step 2430, based on the training model, and the breathing rate associated with the user the processor determines whether the user is experiencing the sleeping disorder.

In step 2440, the processor identifies the user based on at least one of a heart rate associated with the user, or the breathing rate associated with the user, to obtain an identified user. The processor can identify the user by receiving a user ID from a user device associated with the user.

In step 2450, based on identifying the user, the processor retrieves from a database a position associated with the adjustable bed frame and the identified user, where the retrieved position is configured to prevent the user from experiencing the sleeping disorder.

In step 2460, upon said retrieving from the database the position, the processor sends a signal to the adjustable bed frame. The signal includes the position associated with the adjustable bed frame.

Various additional steps described herein can be performed.

Figure 25:
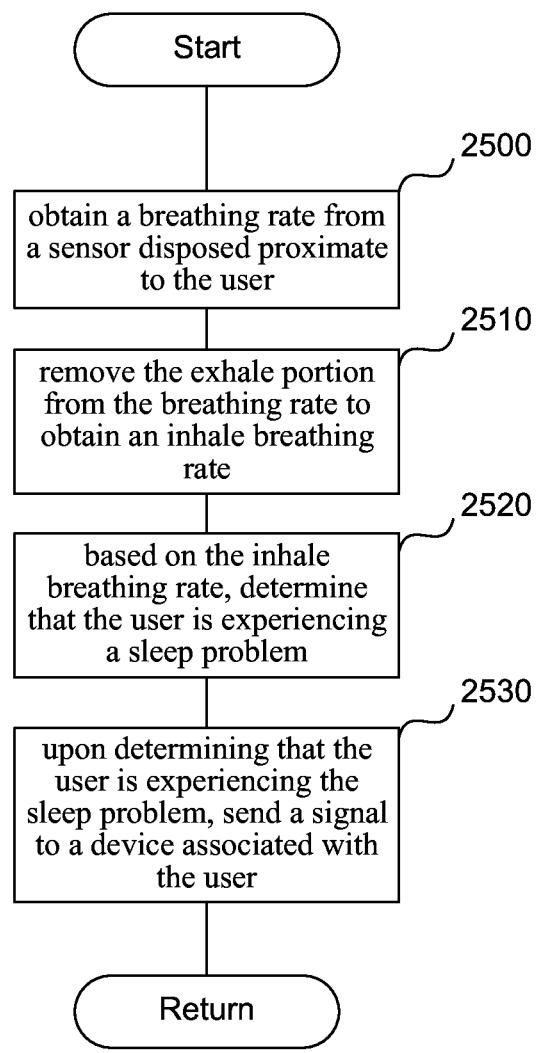
FIG. 25 is a flowchart of a method to detect when a user is experiencing a sleeping disorder, according to one embodiment.

FIG. 25 is a flowchart of a method to detect when a user is experiencing a sleeping disorder, according to one embodiment. In step 2500, the processor obtains a breathing rate from a sensor disposed proximate to the user, such as a piezo sensor, and/or a microphone. The breathing rate includes an inhale portion and an exhale portion.

In step 2510, the processor removes the exhale portion from the breathing rate to obtain an inhale breathing rate.

In step 2520, based on the inhale breathing rate, the processor determines that the user is having the sleeping disorder. Determining that the user is having the sleeping disorder can be done in various ways, some of which are described above, such as detecting the peak frequency indicative of snoring and/or sleep apnea. Determining that the user is having the sleeping disorder can also utilize machine learning, such as deep neural networks.

In one embodiment, the processor receives from a database a first plurality of breathing rates associated with at least one person and a second plurality of breathing rates associated with at least one person. The person can be the user and/or other people whose breathing rates have been measured. Each breathing rate in the first plurality of breathing rates comprises normal breathing. Further, each breathing rate in the first plurality of breathing rates comprises an inhale portion and an exhale portion. Each breathing rate in the second plurality of breathing rates comprises a breathing rate indicative of a sleeping disorder such as snoring and/or sleep apnea. Further, each breathing rate in the second plurality of breathing rates comprises an inhale portion and an exhale portion. The processor removes the exhale portions from each breathing rate in the first and the second plurality of breathing rates to obtain a first plurality of inhale breathing rates, and a second plurality of inhale breathing rates.

Based on the first plurality of inhale breathing rates and the second plurality of inhale breathing rates, the processor creates a training model. The training model is created by providing the first plurality of inhale breathing rates and the second plurality of inhale breathing rates as inputs to create a training model. Creation of the training model can be supervised or unsupervised. In supervised learning, the first plurality of inhale breathing rates provided to the training model can be labeled as normal breathing rates, while the second plurality of inhale breathing rates provided to the training model can be labeled as sleeping disorder breathing rates. In unsupervised learning, the first and second pluralities of inhale breathing rates are unlabeled, and the training model itself determines the categorization.

Finally, based on the training model, and the inhale breathing rate associated with the user, the processor determines that the user is experiencing the sleeping disorder such as snoring and/or sleep apnea.

In step 2520, based on the training model, and the breathing rate associated with the user, the processor determines that the user is having the sleeping disorder.

In step 2530, upon said determining that the user is having the sleeping disorder, the processor sends a signal to a device associated with the user, where the signal includes an indication that the user is experiencing the sleeping disorder. The processor can analyze breathing rate from the piezo sensor and from the microphone separately, or simultaneously. According to one embodiment, if at least one signal includes an indication that the user is experiencing the sleeping disorder the processor sends the signal to the device associated with the user.

According to one embodiment, the processor determines a number of snoring and/or sleep apnea episodes by identifying a time period without the sleeping disorder. In other words, once the processor identifies the occurrence of the sleeping disorder, if the processor identifies the time period in the breathing rate which lasts at least 1 minute, and where that time period is without snoring and/or sleep apnea, the processor increments the number of snoring and/or sleep apnea episodes. When the user awakes, the processor sends a notification to the user device, where the notification includes the number of snoring and/or sleep apnea episodes.

According to another embodiment, once the processor detects snoring and/or sleep apnea, the processor sends a notification to a mobile device associated with the user that the user has been snoring and/or has been having sleep apnea episodes.

The processor can also cause the user device to display a graph of the number of snoring and/or sleep apnea episodes over a specified period of time, such as over the last several days, months, years, etc. The graph can also include an average number of snoring and/or sleep apnea episodes for each day of the week.

In one embodiment, the processor sends the signal to an adjustable bed frame. The adjustable bed frame includes a plurality of adjustable sections. The signal includes an identification associated with the adjustable section, and a position associated with said adjustable section, the position configured to prevent snoring and/or sleep apnea. For example, once the processor detects snoring and/or sleep apnea, the processor sends a signal to the adjustable bed frame to raise the adjustable section corresponding to the user's head.

Various additional steps described herein can be performed.

Figure 26:
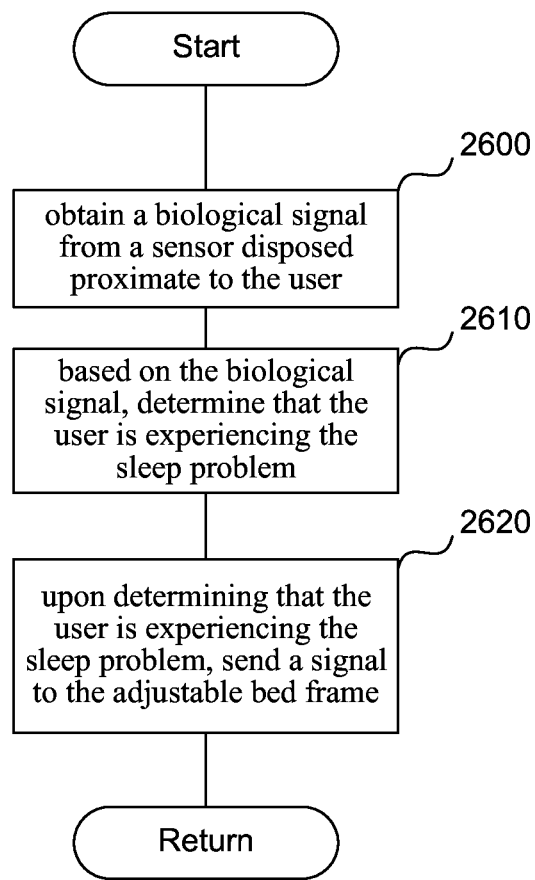
FIG. 26 is a flowchart of a method to adjust an adjustable bed frame upon detecting that a user is experiencing a sleeping disorder, according to one embodiment.

FIG. 26 is a flowchart of a method to adjust an adjustable bed frame upon detecting that a user is experiencing a sleeping disorder, according to one embodiment. In step 2600, the processor obtains a biological signal from a sensor disposed proximate to the user, such as a microphone and/or a piezo sensor. The biological signal includes at least one of a breathing rate associated with the user, a heart rate associated with the user, and a motion associated with the user.

In step 2610, based on the biological signal, the processor determines that the user is experiencing the sleeping disorder, such as snoring and/or sleep apnea. Determining that the user is having the sleeping disorder can be done in various ways, some of which are described above, such as detecting the peak frequency indicative of snoring and/or sleep apnea. Determining that the user is having the sleeping disorder can also utilize machine learning, such as deep neural networks.

In one embodiment, the processor receives from a database a first plurality of biological signals associated with at least one person and a second plurality of biological signals associated with at least one person, wherein each biological signal in the first plurality of biological signals comprises a normal biological signal, and wherein each biological signal in the second plurality of biological signals comprises a biological signal indicative of the sleeping disorder. The person can be the user and/or other people whose biological signals have been measured.

Based on the first plurality of biological signals and the second plurality of biological signals, the processor creates a training model. Creation of the training model can be supervised or unsupervised. In supervised learning, the first plurality of biological signals provided to the training model can be labeled as normal biological signals, while the second plurality of biological signals provided to the training model can be labeled as sleeping disorder biological signals. In unsupervised learning, the first and second pluralities of biological signals are unlabeled, and the training model itself determines the categorization. Based on the training model, and the biological signal associated with the user, the processor determines that the user is experiencing the sleeping disorder.

In step 2620, upon determining that the user is experiencing the sleeping disorder, the processor sends a signal to the adjustable bed frame. The signal includes a position associated with the adjustable bed frame, where the position is configured to prevent the sleeping disorder.

According to one embodiment, the position can be specified by the user. The processor receives from a user device associated with the user an identification (ID) of an adjustable section associated with the adjustable bed frame, and a preferred position associated with the adjustable section. The signal can include the ID of the adjustable section, and the preferred position of the adjustable section, as specified by the user. For example, the adjustable section can correspond to the head, and the preferred position can be a position elevated from the neutral position.

According to another embodiment, the processor automatically determines the adjustable bed frame position to prevent snoring and/or sleep apnea. Once the processor detects snoring and/or sleep apnea, the processor sends to the adjustable bed frame an ID of an adjustable section associated with the adjustable bed frame, and the position associated with the adjustable section. For example, the processor sends the ID of the head section, and a request to rotate the head section by 10° upward. At least one minute after the adjustable bed frame responds to the signal, the processor detects whether the user is experiencing a sleeping disorder such as snoring and/or sleep apnea. If the user is still experiencing the sleeping disorder, the processor again sends the ID of the head section, and a request to rotate the head section by 10° upward. The processor iteratively adjusts the height of the head section, until the user stops experiencing the sleeping disorder.

Once the processor no longer detects the sleeping disorder, the processor stores the current position of the adjustable bed frame in a database. The processor can in the future retrieve the stored position, and, whenever the sleeping disorder is detected, send the stored position to the adjustable bed frame to prevent snoring and/or sleep apnea.

According to one embodiment, the processor identifies the user based on the breathing rate associated with the user to obtain a user ID. According to another embodiment, the processor receives the user ID from a device associated with the user. Based on the user ID, the processor retrieves from the database a position associated with the adjustable bed frame and with the user ID. The position is configured to prevent snoring and/or sleep apnea, and can be calculated by the processor as described herein, or can be specified by the user as described herein.

Various additional steps described herein can be performed.

Figure 27:
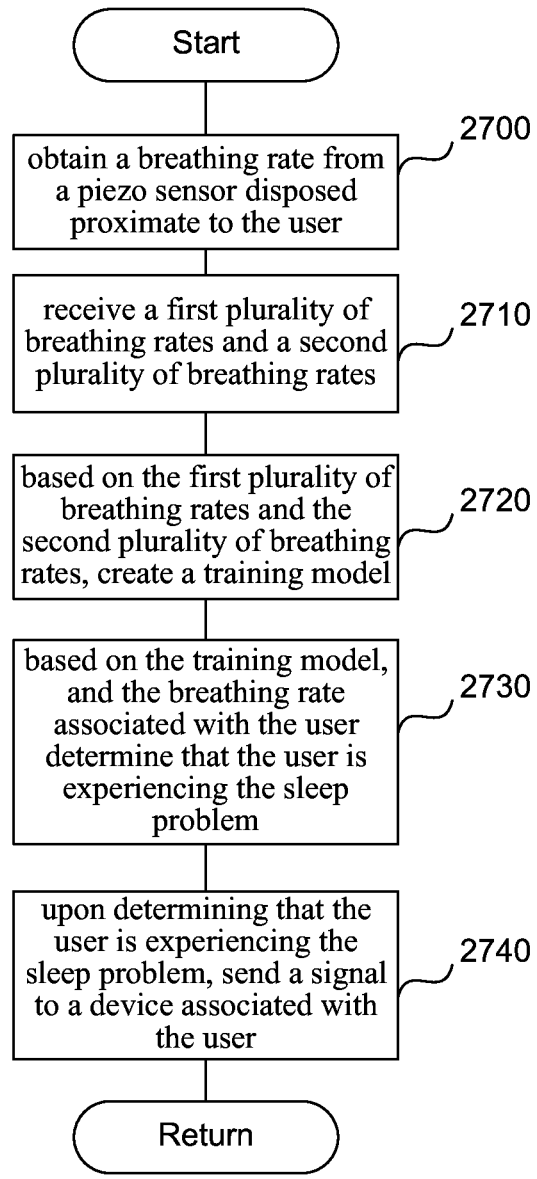
FIG. 27 is a flowchart of a method to send a signal to a device associated with the user upon detecting that the user is experiencing a sleeping disorder, according to one embodiment.

FIG. 27 is a flowchart of a method to send a signal to a device associated with the user upon detecting that the user is experiencing a sleeping disorder, according to one embodiment. In step 2700, a piezo sensor disposed proximate to the user measures a breathing rate associated with the user, wherein the breathing rate comprises an inhale portion and an exhale portion.

In step 2710, a processor receives from a database a first plurality of breathing rates associated with at least one person and a second plurality of breathing rates associated with at least one person. Each breathing rate in the first plurality of breathing rates includes normal breathing. Each breathing rate in the second plurality of breathing rates includes breathing indicative of the sleeping disorder.

In step 2720, based on the first plurality of breathing rates and the second plurality of breathing rates, the processor creates a training model. The training model is created by providing the first plurality of breathing rates and the second plurality of breathing rates as inputs to create a training model. Creation of the training model can be supervised or unsupervised. In supervised learning, the first plurality of breathing rates provided to the training model can be labeled as normal breathing rates, while the second plurality of breathing rates provided to the training model can be labeled as sleeping disorder breathing rates. In unsupervised learning, the first and second pluralities of breathing rates are unlabeled, and the training model itself determines the categorization.

Creating the training model can include additional steps. In one embodiment, the first and the second pluralities of breathing rates are preprocessed before providing inputs to create the training model. Each breathing rate includes an inhale portion and an exhale portion. The exhale portion in each of the breathing rates in the first and the second pluralities of breathing rates is removed to obtain a first plurality of inhale breathing rates, and a second plurality of inhale breathing rates. The first plurality of inhale breathing rates and the second plurality of inhale breathing rates are then used as inputs to create the training model.

In step 2730, based on the training model, and the breathing rate associated with the user, the processor determines that the user is experiencing the sleeping disorder, such as snoring and/or sleep apnea. In one embodiment, the breathing rate is preprocessed to remove the exhale portion to obtain an inhale breathing rate associated with the user. Based on the training model built on the first and second pluralities of inhale breathing rates, and the inhale breathing rate associated with the user, the processor determines whether the user is experiencing the sleeping disorder.

In step 2740, upon said determining that the user is experiencing the sleeping disorder, the processor sends a signal to a device associated with the user. The signal includes an indication that the user is experiencing the sleeping disorder.

According to one embodiment, in addition, the processor determines a number of snoring and/or sleep apnea episodes by identifying a time period without the sleeping disorder. In other words, once the processor identifies the occurrence of the sleeping disorder, if the processor identifies the time period in the breathing rate which lasts at least 1 minute, and where that time period is without snoring and/or sleep apnea, the processor increments the number of snoring and/or sleep apnea episodes. When the user awakes, the processor sends a notification to the user device, where the notification includes the number of snoring and/or sleep apnea episodes.

In one embodiment, the processor automatically determines the adjustable bed frame position to prevent snoring and/or sleep apnea. Once the processor detects snoring and/or sleep apnea, the processor sends to the adjustable bed frame an ID of an adjustable section associated with the adjustable bed frame, and the position associated with the adjustable section. For example, the processor sends the ID of the head section, and a request to rotate the head section by 10° upward. At least one minute after the adjustable bed frame responds to the signal, the processor detects whether the user is experiencing a sleeping disorder such as snoring and/or sleep apnea. If the user is still experiencing the sleeping disorder, the processor again sends the ID of the head section, and a request to rotate the head section by 10° upward. The processor iteratively adjusts the height of the head section, until the user stops experiencing the sleeping disorder.

Once the processor no longer detects the sleeping disorder, the processor stores the current position of the adjustable bed frame in a database. The processor can in the future retrieve the stored position, and, whenever the sleeping disorder is detected, send the stored position to the adjustable bed frame to prevent snoring and/or sleep apnea.

Various additional steps described herein can be performed.

Computer

Figure 28:
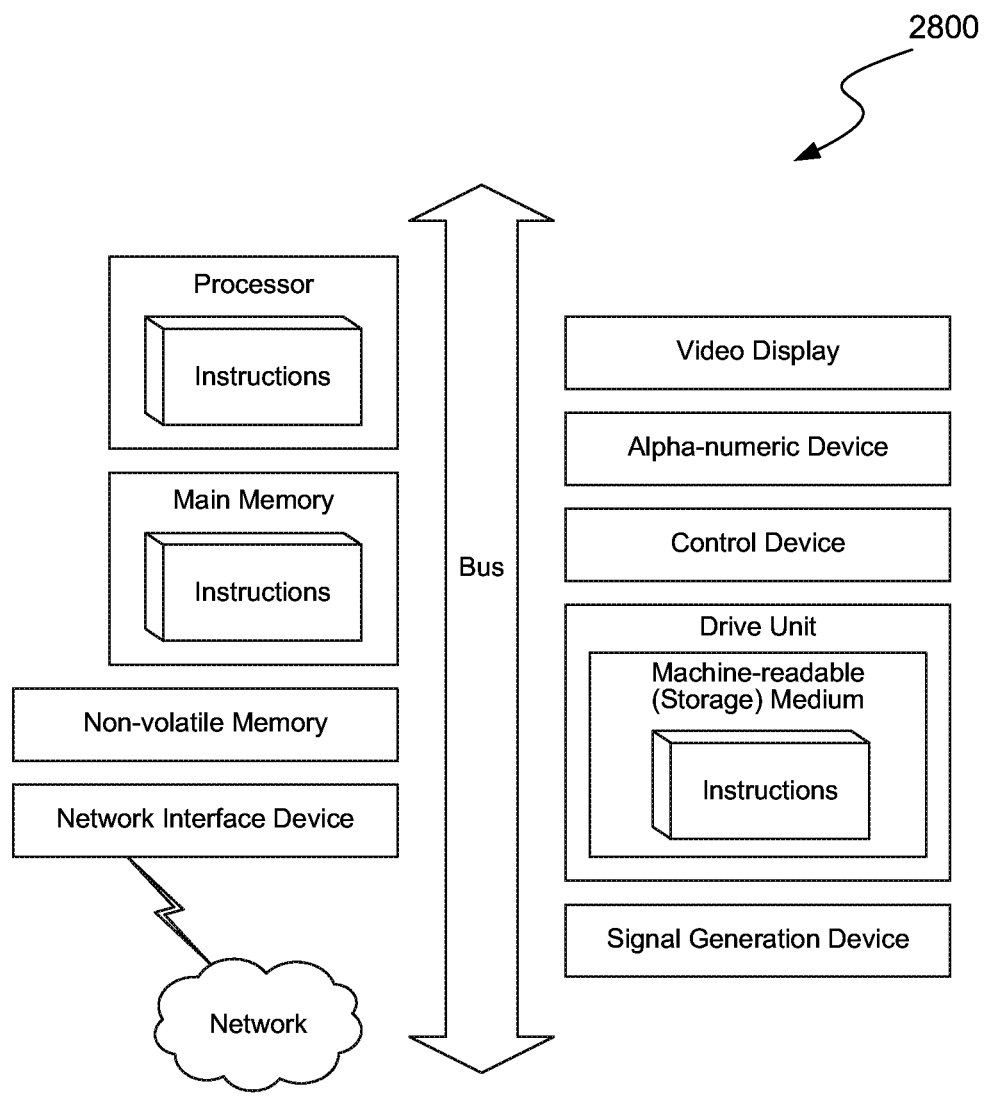
FIG. 28 is a diagrammatic representation of a machine in the example form of a computer system 2800 within which a set of instructions, for causing the machine to perform any one or more of the methodologies or modules discussed herein, may be executed.

FIG. 28 is a diagrammatic representation of a machine in the example form of a computer system 2800 within which a set of instructions, for causing the machine to perform any one or more of the methodologies or modules discussed herein, may be executed.

In the example of FIG. 28, the computer system 2800 includes a processor, memory, non-volatile memory, and an interface device. Various common components (e.g., cache memory) are omitted for illustrative simplicity. The computer system 2800 is intended to illustrate a hardware device on which any of the components described in the example of FIGS. 1-27 (and any other components described in this specification) can be implemented. The computer system 2800 can be of any applicable known or convenient type. The components of the computer system 2800 can be coupled together via a bus or through some other known or convenient device.

This disclosure contemplates the computer system 2800 taking any suitable physical form. As example and not by way of limitation, computer system 2800 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, or a combination of two or more of these. Where appropriate, computer system 2800 may include one or more computer systems 2800; be unitary or distributed; span multiple locations; span multiple machines; or reside in a cloud, which may include one or more cloud components in one or more networks. Where appropriate, one or more computer systems 2800 may perform without substantial spatial or temporal limitation one or more steps of one or more methods described or illustrated herein. As an example and not by way of limitation, one or more computer systems 2800 may perform in real time or in batch mode one or more steps of one or more methods described or illustrated herein. One or more computer systems 2800 may perform at different times or at different locations one or more steps of one or more methods described or illustrated herein, where appropriate.

The processor may be, for example, a conventional microprocessor such as an Intel Pentium microprocessor or Motorola power PC microprocessor. One of skill in the relevant art will recognize that the terms "machine-readable (storage) medium" or "computer-readable (storage) medium" include any type of device that is accessible by the processor.

The memory is coupled to the processor by, for example, a bus. The memory can include, by way of example but not limitation, random access memory (RAM), such as dynamic RAM (DRAM) and static RAM (SRAM). The memory can be local, remote, or distributed.

The bus also couples the processor to the non-volatile memory and drive unit. The non-volatile memory is often a magnetic floppy or hard disk, a magnetic-optical disk, an optical disk, a read-only memory (ROM), such as a CD-ROM, EPROM, or EEPROM, a magnetic or optical card, or another form of storage for large amounts of data. Some of this data is often written, by a direct memory access process, into memory during execution of software in the computer 2800. The non-volatile storage can be local, remote, or distributed. The non-volatile memory is optional because systems can be created with all applicable data available in memory. A typical computer system will usually include at least a processor, memory, and a device (e.g., a bus) coupling the memory to the processor.

Software is typically stored in the non-volatile memory and/or the drive unit. Indeed, storing an entire large program in memory may not even be possible. Nevertheless, it should be understood that for software to run, if necessary, it is moved to a computer-readable location appropriate for processing, and for illustrative purposes, that location is referred to as the memory in this paper. Even when software is moved to the memory for execution, the processor will typically make use of hardware registers to store values associated with the software, and local cache that, ideally, serves to speed up execution. As used herein, a software program is assumed to be stored at any known or convenient location (from non-volatile storage to hardware registers) when the software program is referred to as "implemented in a computer-readable medium." A processor is considered to be "configured to execute a program" when at least one value associated with the program is stored in a register readable by the processor.

The bus also couples the processor to the network interface device. The interface can include one or more of a modem or network interface. It will be appreciated that a modem or network interface can be considered to be part of the computer system 2800. The interface can include an analog modem, ISDN modem, cable modem, token ring interface, satellite transmission interface (e.g., "direct PC"), or other interfaces for coupling a computer system to other computer systems. The interface can include one or more input and/or output devices. The I/O devices can include, by way of example but not limitation, a keyboard, a mouse or other pointing device, disk drives, printers, a scanner, and other input and/or output devices, including a display device. The display device can include, by way of example but not limitation, a cathode ray tube (CRT), liquid crystal display (LCD), or some other applicable known or convenient display device. For simplicity, it is assumed that controllers of any devices not depicted in the example of FIG. 28 reside in the interface.

In operation, the computer system 2800 can be controlled by operating system software that includes a file management system, such as a disk operating system. One example of operating system software with associated file management system software is the family of operating systems known as Windows® from Microsoft Corporation of Redmond, Wash., and its associated file management systems. Another example of operating system software with its associated file management system software is the Linux™ operating system and its associated file management system. The file management system is typically stored in the non-volatile memory and/or drive unit and causes the processor to execute the various acts required by the operating system to input and output data and to store data in the memory, including storing files on the non-volatile memory and/or drive unit.

Some portions of the detailed description may be presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from the following discussion, it is appreciated that, throughout the description, discussions utilizing terms such as "processing" or "computing" or "calculating" or "determining" or "displaying" or "generating" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The algorithms and displays presented herein are not inherently related to any particular computer or other apparatus. Various general purpose systems may be used with programs in accordance with the teachings herein, or it may prove convenient to construct more specialized apparatus to perform the methods of some embodiments. The required structure for a variety of these systems will appear from the description below. In addition, the techniques are not described with reference to any particular programming language, and various embodiments may thus be implemented using a variety of programming languages.

In alternative embodiments, the machine operates as a standalone device or may be connected (e.g., networked) to other machines. In a networked deployment, the machine may operate in the capacity of a server or a client machine in a client-server network environment, or as a peer machine in a peer-to-peer (or distributed) network environment.

The machine may be a server computer, a client computer, a personal computer (PC), a tablet PC, a laptop computer, a set-top box (STB), a personal digital assistant (PDA), a cellular telephone, an iPhone, a Blackberry, a processor, a telephone, a web appliance, a network router, switch or bridge, or any machine capable of executing a set of instructions (sequential or otherwise) that specify actions to be taken by that machine.

While the machine-readable medium or machine-readable storage medium is shown in an exemplary embodiment to be a single medium, the terms "machine-readable medium" and "machine-readable storage medium" should be taken to include a single medium or multiple media (e.g., a centralized or distributed database, and/or associated caches and servers) that store the one or more sets of instructions. The terms "machine-readable medium" and "machine-readable storage medium" shall also be taken to include any medium that is capable of storing, encoding or carrying out a set of instructions for execution by the machine and that cause the machine to perform any one or more of the methodologies or modules of the presently disclosed technique and innovation.

In general, the routines executed to implement the embodiments of the disclosure may be implemented as part of an operating system or a specific application, component, program, object, module or sequence of instructions referred to as "computer programs." The computer programs typically comprise one or more instructions set at various times in various memory and storage devices in a computer, and that, when read and executed by one or more processing units or processors in a computer, cause the computer to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Further examples of machine-readable storage media, machine-readable media, or computer-readable (storage) media include but are not limited to recordable type media such as volatile and non-volatile memory devices, floppy and other removable disks, hard disk drives, optical disks (e.g., Compact Disk Read-Only Memory (CD ROMS), Digital Versatile Disks, (DVDs), etc.), among others, and transmission type media, such as digital and analog communication links.

In some circumstances, operation of a memory device, such as a change in state from a binary one to a binary zero or vice-versa, for example, may comprise a transformation, such as a physical transformation. With particular types of memory devices, such a physical transformation may comprise a physical transformation of an article to a different state or thing. For example, but without limitation, for some types of memory devices, a change in state may involve an accumulation and storage of charge or a release of stored charge. Likewise, in other memory devices, a change of state may comprise a physical change or transformation in magnetic orientation or a physical change or transformation in molecular structure, such as from crystalline to amorphous or vice-versa. The foregoing is not intended to be an exhaustive list of all examples in which a change in state from a binary one to a binary zero or vice-versa in a memory device may comprise a transformation, such as a physical transformation. Rather, the foregoing is intended as illustrative examples.

A storage medium typically may be non-transitory or comprise a non-transitory device. In this context, a non-transitory storage medium may include a device that is tangible, meaning that the device has a concrete physical form, although the device may change its physical state. Thus, for example, non-transitory refers to a device remaining tangible despite this change in state.

Remarks

In many of the embodiments disclosed in this application, the technology is capable of allowing multiple different users to use the same piece of furniture equipped with the presently disclosed technology. For example, different people can sleep in the same bed. In addition, two different users can switch the side of the bed that they sleep on, and the technology disclosed here will correctly identify which user is sleeping on which side of the bed. The technology identifies the users based on any of the following signals alone or in combination: heart rate, breathing rate, body motion, or body temperature associated with each user. In another embodiment, the technology disclosed here identifies the user by receiving both the user ID and side of the bed associated with the user ID, from a device associated with the user.

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling others skilled in the relevant art to understand the claimed subject matter, the various embodiments, and the various modifications that are suited to the particular uses contemplated.

While embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Although the above Detailed Description describes certain embodiments and the best mode contemplated, no matter how detailed the above appears in text, the embodiments can be practiced in many ways. Details of the systems and methods may vary considerably in their implementation details, while still being encompassed by the specification. As noted above, particular terminology used when describing certain features or aspects of various embodiments should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless those terms are explicitly defined herein. Accordingly, the actual scope of the invention encompasses not only the disclosed embodiments, but also all equivalent ways of practicing or implementing the embodiments under the claims.

The language used in the specification has been principally selected for readability and instructional purposes, and it may not have been selected to delineate or circumscribe the inventive subject matter. It is therefore intended that the scope of the invention be limited not by this Detailed Description, but rather by any claims that issue on an application based hereon. Accordingly, the disclosure of various embodiments is intended to be illustrative, but not limiting, of the scope of the embodiments, which is set forth in the following claims.

The invention claimed is:

1. A method to detect when a user is experiencing a sleeping disorder, the method comprising:
   obtaining a breathing rate from a sensor disposed proximate to the user, the breathing rate comprising an inhale portion and an exhale portion;
   identifying an inhale breathing rate of the user by removing the exhale portion from the breathing rate to obtain the inhale portion as the inhale breathing rate of the user;
   based on the inhale breathing rate of the user, determining that the user is experiencing the sleeping disorder, wherein determining that the user is experiencing the sleeping disorder includes:
     determining frequencies corresponding with the inhale breathing rate,
     determining that the frequencies include a first frequency range around a first peak frequency and a second frequency range around a second peak frequency, the first frequency range being different than the second frequency range, and
     determining that the first frequency range is within a frequency range corresponding to the sleeping disorder, and that the second frequency range is not within the frequency range corresponding to the sleeping disorder, wherein determining that the user is experiencing the sleeping disorder is based on the first peak frequency and the first frequency range; and
   upon said determining that the user is experiencing the sleeping disorder, sending a signal to a device associated with the user, the signal comprising an indication that the user is experiencing the sleeping disorder.

2. The method of claim 1, said determining that the user is experiencing the sleeping disorder comprising:
   receiving a first plurality of breathing rates associated with at least one person and a second plurality of breathing rates associated with the at least one person, wherein each breathing rate in the first plurality of breathing rates comprises normal breathing and further each breathing rate in the first plurality of breathing rates comprises the inhale portion and the exhale portion, and wherein each breathing rate in the second plurality of breathing rates comprises snoring and further each breathing rate in the second plurality of breathing rates comprises the inhale portion and the exhale portion;
   removing the exhale portion from each breathing rate in the first plurality of breathing rates and the second plurality of breathing rates to obtain a first plurality of inhale breathing rates and a second plurality of inhale breathing rates;
   based on the first plurality of inhale breathing rates and the second plurality of inhale breathing rates, creating a training model; and
   based on the training model, and the inhale breathing rate associated with the user, determining that the user is snoring.

3. The method of claim 1, said determining that the user is experiencing the sleeping disorder comprising:
   receiving a first plurality of breathing rates associated with at least one person and a second plurality of breathing rates associated with the at least one person, wherein each breathing rate in the first plurality of breathing rates comprises normal breathing and further each breathing rate in the first plurality of breathing rates comprises the inhale portion and the exhale portion, and wherein each breathing rate in the second plurality of breathing rates comprises breathing indicative of sleep apnea and further each breathing rate in the second plurality of breathing rates comprises the inhale portion and the exhale portion;
   removing the exhale portion from each breathing rate in the first plurality of breathing rates and the second plurality of breathing rates to obtain a first plurality of inhale breathing rates and a second plurality of inhale breathing rates;
   based on the first plurality of inhale breathing rates and the second plurality of inhale breathing rates, creating a training model; and
   based on the training model, and the inhale breathing rate associated with the user, determining that the user is experiencing sleep apnea.

4. The method of claim 1, said determining that the user is experiencing the sleeping disorder comprising:
   transforming the inhale breathing rate to obtain a transformed breathing rate comprising a plurality of frequencies and a plurality of intensities associated with the plurality of frequencies; and
   detecting a peak frequency in the plurality of frequencies associated with the transformed breathing rate, wherein the peak frequency is indicative of the sleeping disorder.

5. The method of claim 4, said detecting the peak frequency indicative of the sleeping disorder comprising:
   detecting an intensity peak in the plurality of intensities, wherein the intensity peak is associated with the peak frequency; and
   when the peak frequency associated with the intensity peak is within a snoring frequency range, determining that the peak frequency is indicative of snoring, the snoring frequency range comprising frequencies within 0 Hz to 150 Hz.

6. The method of claim 4, said detecting the peak frequency indicative of the sleeping disorder comprising:
   smoothing the transformed breathing rate to obtain a smooth transformed breathing rate, the smooth transformed breathing rate comprising a plurality of smooth frequencies, and a plurality of smooth intensities associated with the plurality of smooth frequencies; and
   detecting an intensity peak in the plurality of smooth intensities, wherein the intensity peak is associated with the peak frequency; and
   when the peak frequency associated with the intensity peak is within a snoring frequency range, determining that the peak frequency is indicative of snoring, the snoring frequency range comprising frequencies within 0 Hz to 150 Hz.

7. The method of claim 4, further comprising:

determining a frequency band around the peak frequency, wherein the frequency band comprises a continuous frequency region around the peak frequency, the continuous frequency region comprising frequencies whose corresponding intensities differ less than 3 dB from an intensity associated with the peak frequency;

selecting the peak frequency and the frequency band, wherein the frequency band is greater than 1 Hz; and based on the peak frequency and the frequency band, detecting sleep apnea.

8. The method of claim 1, further comprising:

determining a number of snoring episodes experienced by the user, said determining the number of snoring episodes comprising:

identifying a time period associated with the breathing rate, wherein the time period lasts at least 1 minute, and wherein the time period is free of snoring; and incrementing an indication of the number of snoring episodes experienced by the user.

9. The method of claim 8, said sending the signal to the device associated with the user comprising:

sending a notification comprising the number of snoring episodes.

10. The method of claim 1, said sending the signal to the device associated with the user comprising:

sending a notification to a mobile device associated with the user that the user has been snoring.

11. The method of claim 1, said sending the signal to the device associated with the user comprising:

sending the signal to an adjustable bed frame, the adjustable bed frame comprising an adjustable section, the signal comprising an identification associated with the adjustable section, and a position associated with the adjustable section, the position configured to prevent snoring.

* * * * *